United States Patent
Allen et al.

(10) Patent No.: US 7,115,654 B2
(45) Date of Patent: Oct. 3, 2006

(54) CASPASE-1 INHIBITORS AND METHODS FOR THEIR USE

(75) Inventors: Darin Allen, San Carlos, CA (US); Bruce Fahr, San Carlos, CA (US); Johan Oslob, Sunnyvale, CA (US); Brian C. Raimundo, San Francisco, CA (US); Michael J. Romanowski, Foster City, CA (US)

(73) Assignee: Sunesis Pharmaceuticals, Inc., South San Francisco, CA (US)

( * ) Notice: Subject to any disclaimer, the term of this patent is extended or adjusted under 35 U.S.C. 154(b) by 167 days.

(21) Appl. No.: 10/456,458

(22) Filed: Jun. 5, 2003

(65) Prior Publication Data

US 2004/0048895 A1      Mar. 11, 2004

Related U.S. Application Data

(60) Provisional application No. 60/386,501, filed on Jun. 5, 2002.

(51) Int. Cl.
*A61K 31/38*     (2006.01)
*C07D 333/10*    (2006.01)

(52) U.S. Cl. ............... 514/448; 546/135; 546/115; 549/72; 549/6; 544/349

(58) Field of Classification Search ............... 544/349, 544/356; 546/251, 135, 115; 549/59, 60, 549/76, 77, 441, 72, 6; 562/442; 514/249, 514/300, 438, 444, 563, 448
See application file for complete search history.

(56) References Cited

U.S. PATENT DOCUMENTS

| | | | |
|---|---|---|---|
| 6,153,591 A | 11/2000 | Cai et al. ............. | 514/19 |
| 6,204,261 B1 | 3/2001 | Batchelor et al. ........ | 514/221 |
| 6,566,338 B1 | 5/2003 | Weber et al. ............ | 514/19 |
| 6,878,743 B1* | 4/2005 | Choong et al. ........... | 514/448 |
| 2004/0048797 A1* | 3/2004 | Miller et al. ............ | 514/12 |

FOREIGN PATENT DOCUMENTS

| | | |
|---|---|---|
| WO | WO 99/56765 | 11/1999 |
| WO | WO 02/094263 | 11/2002 |
| WO | WO 03/024955 | 3/2003 |

OTHER PUBLICATIONS

International Search Report for PCT/US03/18021, mailed on May 27, 2004, 4 pages.
Relton et al., (1992) *Brain Research Bulletin*, 29:243-246.
Elford et al., (1995) *British Journal of Pharmacology* 115:601-606.
Miura et al., (1993) *Cell*, 75:653-660.
Alnerni et al., (1996) *Cell*, 87:171.
Thornberry et al., (1997) *J. Biol. Chem.* 272:17907-17911.
Ghayur et al. (1997) *Nature* 386:619-623.

* cited by examiner

*Primary Examiner*—Cecilia J. Tsang
*Assistant Examiner*—James Balls
(74) *Attorney, Agent, or Firm*—Brenda Herschbach Jarrell; Nadège M Lagneau; Choate, Hall & Stewart, LLP

(57) ABSTRACT

The invention provides compounds of Formula I and derivatives thereof, pharmaceutical compositions comprising a compound of Formula I, and methods of treatment utilizing such compounds and compositions:

Formula I

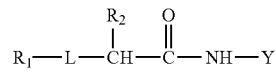

wherein:
$R_1$ is chosen from optionally substituted aryl, optionally substituted aralkyl, optionally substituted heteroaryl, and optionally substituted heteroaralkyl;
L is a linker;
$R_2$ is chosen from optionally substituted aryl, optionally substituted aralkyl, optionally substituted heteroaryl, and optionally substituted heteroaralkyl; and Y is 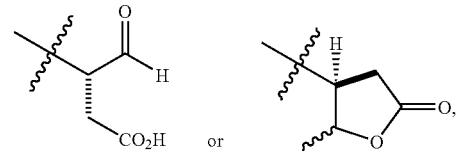

or single stereoisomers, mixtures of stereoisomers, or the pharmaceutically acceptable salts, amides, or esters thereof.

21 Claims, No Drawings

CASPASE-1 INHIBITORS AND METHODS FOR THEIR USE

This application claims priority to U.S. provisional application No. 60/386,501, filed Jun. 5, 2002, which is incorporated herein by this reference in its entirety.

FIELD OF THE INVENTION

This invention relates to compounds which are inhibitors of caspase-1 (also known as interleukin-1-B converting enzyme or ICE) and are useful in reducing or treating apoptotic cell death and/or reducing interleukin 1-β or interferon-gamma production.

BACKGROUND OF THE INVENTION

Mammalian interleukin-1β. (IL-1β) plays an important role in various pathologic processes, including chronic and acute inflammation and autoimmune diseases. IL-1β is synthesized as a cell associated precursor polypeptide (pro-IL-1β) that is unable to bind IL-1 receptors and is biologically inactive. By inhibiting conversion of precursor IL-1β to mature IL-1β, the activity of interleukin-1 can be inhibited.

Interleukin-1β converting enzyme (ICE) is a protease responsible for the activation of interleukin-1β (IL-1β). ICE is a substrate-specific cysteine protease that cleaves the inactive prointerleukin-1 to produce the mature IL-1. The genes that encode for ICE and CPP32 are members of the mammalian ICE/Ced-3 family of genes which presently includes at least twelve members: ICE, CPP32/Yama/Apopain, mICE2, ICE4, ICH1, TX/ICH-2, MCH2, MCH3, MCH4, FLICE/MACH/MCH5, ICE-LAP6 and $ICE_{rel}$ III. The proteolytic activity of this family of cysteine proteases, whose active site (a cysteine residue) is essential for ICE-mediated apoptosis, appears critical in mediating cell death (Miura et al., *Cell* 75:653–660 (1993)). This gene family has recently been named caspases (Alnernri et al., *Cell*, 87:171 (1996), and Thornberry et al., *J. Biol. Chem.* 272:17907–17911 (1997)) and divided into three groups according to its known functions.

Agents that modulate IL-1β activity have been shown to have beneficial in vivo effects. For example, compounds that are interleukin-1 receptor antagonists have been shown to inhibit ischemic and excitotoxic damage in rat brains (e.g., Relton et al. (1992) *Brain Research Bulletin* (1992) 29:243–246). Additionally, ICE inhibitors were shown to reduce inflammation and pyrexia in rats (Elford et al. (1995) *British Journal of Pharmacology* 115:601–606).

In addition to its effects on IL-1β, ICE has been shown to place a role in the production of the inflammatory mediator interferon-gamma (Ghayur et al. (1997) *Nature* 386:619–623). ICE processes the inactive proform of interferon-gamma (IGIF; interleukin-18) to active IGIF, a protein that induces production of interferon-gamma by T-cells and natural killer cells. Interferon-gamma has been implicated in the pathogenesis of diseases such as inflammatory disorders and septic shock. Therefore, inhibitors of caspase-1 would be expected to have beneficial effects in such disease states.

Many potent caspase inhibitors have been prepared based on the peptide substrate structures of caspases. However, the need exists for improved caspase-1 inhibitors. These inhibitors thus can be employed as therapeutic agents to treat disease states in which regulated cell death and the cytokine activity of IL-1 or IGIF play a role. Accordingly, it is an object of the present invention to provide methods and compositions useful in the inhibition of caspase-1.

SUMMARY OF THE INVENTION

The invention relates to the discovery that the compounds represented by Formula I and in particular Formula II or Formula III below are inhibitors of caspase-1. The invention also relates to the use of the compounds of the invention for treating conditions that are mediated by caspase-1 activity, such as for reducing, preventing or treating maladies in which apoptotic cell death or cytokine activity of IL-1 or IGIF is either a causative factor or a result. Examples of uses for the present invention include protecting the nervous system following focal ischemia and global ischemia; treating neurodegenerative disorders such as Alzheimer's disease, Huntington's Disease, prion diseases, Parkinson's Disease, multiple sclerosis, amyotrophic lateral sclerosis, ataxia, telangiectasia, and spinobulbar atrophy; treating heart disease including myocardial infarction, congestive heart failure and cardiomyopathy; treating retinal disorders; treating autoimmune disorders including lupus erythematosus, rheumatoid arthritis, type 1 diabetes, Sjogren's syndrome and glomerulonephritis; treating polycystic kidney disease and anemia/erythropoiesis; treating immune system disorders, including AIDS and SCIDS; treating or ameliorating sepsis, reducing or preventing cell, tissue and organ damage during transplantation; reducing or preventing cell line death in industrial biotechnology; reducing or preventing alopecia (hair loss); and reducing the premature death of skin cells. The present invention provides pharmaceutical compositions comprising a compound of Formula I, preferably Formula II or Formula III in an effective amount to reduce apoptotic cell death in an animal.

The present invention also provides preservation or storage solutions for mammalian organs or tissue, or growth media for mammalian or yeast cells, wherein an effective amount of a compound of Formula I, preferably Formula II or Formula III is included in said solutions or media in order to reduce apoptotic cell death in said organs, tissue or cells.

The methods employ compounds represented by Formula I and particularly Formula II or Formula III:

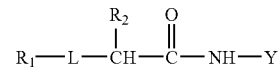

Formula I wherein:

$R_1$ is chosen from optionally substituted aryl, optionally substituted aralkyl, optionally substituted heteroaryl, and optionally substituted heteroaralkyl;

L is a linker;

$R_2$ is chosen from optionally substituted aryl, optionally substituted aralkyl, optionally substituted heteroaryl, and optionally substituted heteroaralkyl; and Y is 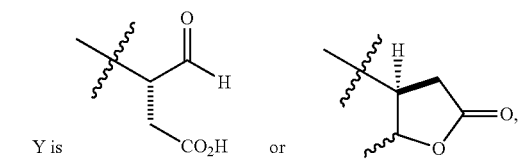

or single stereoisomers, mixtures of stereoisomers, or the pharmaceutically acceptable salts, amides, or esters thereof;

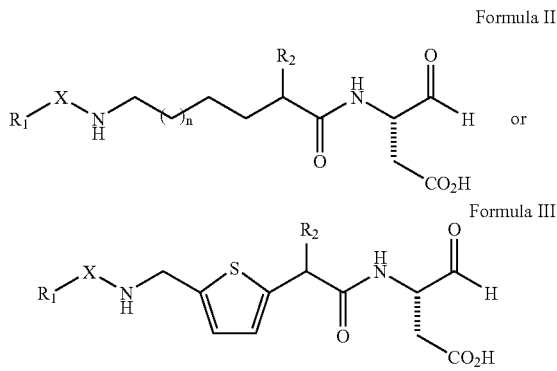

wherein:

R₁ is chosen from optionally substituted aryl, optionally substituted aralkyl, optionally substituted heteroaryl, and optionally substituted heteroaralkyl;

R₂ is chosen from optionally substituted aryl, optionally substituted aralkyl, optionally substituted heteroaryl, and optionally substituted heteroaralkyl;

X is —(CO)— or —(SO₂)—; and n is 0 or 1;

including stereoisomers, mixtures of stereoisomers, or the pharmaceutically acceptable salts, amides, or esters thereof.

The invention also relates to a pharmaceutical composition containing a therapeutically effective amount of a compound of Formula I and in particular Formula II or Formula III, or a pharmaceutically acceptable salt, amide, or ester thereof admixed with at least one pharmaceutically acceptable excipient. In one embodiment, a compound of the invention constitutes the active principle of the formulation. In another embodiment, the compounds are combined with other active compounds, such as those that are used to treat inflammation, rheumatoid arthritis, and sepsis.

The invention is also directed to crystalline apo-human caspase-1.

DETAILED DESCRIPTION OF THE INVENTION

Definitions

As used in the present specification, the following words and phrases are generally intended to have the meanings as set forth below, except to the extent that the context in which they are used indicates otherwise. The following abbreviations and terms have the indicated meanings throughout:

| | |
|---|---|
| Ac = | acetyl |
| AcOH = | acetic acid |
| Boc = | t-butyloxy carbonyl |
| Bn = | benzyl |
| Bu = | butyl |
| c- = | cyclo |
| DCM = | dichloromethane = methylene chloride = CH₂Cl₂ |
| DIEA = | N,N-diisopropylethylamine |
| DMF = | N,N-dimethylformamide |
| DMSO = | dimethyl sulfoxide |
| EDC = | 1-(3-dimethylaminopropyl)-3-ethylcarbodiimide hydrochloride |
| Et = | ethyl |
| EtOAc = | ethyl acetate |
| EtOH = | ethanol |
| Fmoc = | 9-fluorenylmethoxycarbonyl |
| Fmoc-OSu = | (9-fluorenylmethoxycarbonyloxy)succinimide |
| GC = | gas chromatography |
| h = | hour |
| HOBt = | hydroxybenzotriazole |
| Me = | methyl |
| min = | minute |
| mL = | milliliter |
| NHAc = | acetyl amino |
| Ph = | phenyl |
| PG = | protecting group |
| Py = | pyridine |
| PyBOP = | benzotriazol-1-yl-oxytripyrrolidinophosphonium hexafluorophosphate |
| PyBroP = | bromo-tris-pyrrolidino-phosphonium hexafluorophosphate |
| rt = | room temperature |
| sat'd = | saturated |
| s- = | secondary |
| t- = | tertiary |
| TFA = | trifluoroacetic acid |
| THF = | tetrahydrofuran |
| TLC = | thin layer chromatography |

Alkyl is intended to include linear, branched, or cyclic hydrocarbon structures and combinations thereof. Lower alkyl refers to alkyl groups of from 1 to 5 carbon atoms. Examples of lower alkyl groups include methyl, ethyl, propyl, isopropyl, butyl, s-and t-butyl and the like. Preferred alkyl groups are those of $C_{20}$ or below. More preferred alkyl groups are those of $C_{13}$ or below. Cycloalkyl is a subset of alkyl and includes cyclic hydrocarbon groups of from 3 to 13 carbon atoms. Examples of cycloalkyl groups include c-propyl, c-butyl, c-pentyl, norbornyl, adamantyl and the like. In this application, alkyl refers to alkanyl, alkenyl and alkynyl residues; it is intended to include cyclohexylmethyl, vinyl, allyl, isoprenyl and the like. Alkylene is another subset of alkyl, referring to the same residues as alkyl, but having two points of attachment. Examples of alkylene include ethylene (—CH₂CH₂—), propylene (—CH₂CH₂CH₂—), dimethylpropylene (—CH₂C(CH₃)₂CH₂—) and cyclohexylpropylene (—CH₂CH₂CH(C₆H₁₃)—). When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. Preferred alkyl groups are methyl, isopropyl and cyclopentyl.

Alkylene when defined as —(CH₂)ₘ— or —(CH₂)ₙ— where m and n are an integer refers to a saturated moiety which is similar to alkyl except that it is attached to the parent structure using two bonds. Alkenylene and alkynylene are alkylene moieties which contain one or more double or triple bonds respectively.

Alkoxy or alkoxyl refers to the group —O-alkyl, preferably including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Acetal refers to a compound formed by addition of an alcohol (R'OH) to an aldehyde moiety, often with an acid catalyst. If the aldehyde reacts with one equivalent of an alcohol, a hemiacetal is formed. If the aldehyde reacts with two equivalents of an alcohol, the acetal is formed. Acetals or hemiacetals also may be formed through the intramolecular cyclization of an aldehyde with either an alcohol or carboxy group.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Amino refers to the group —$NH_2$. Substituted amino refers to the group —NHR or —NRR where each R is independently selected from the group: optionally substituted alkyl, optionally substituted alkoxy, optionally substituted amino, optionally substituted aryl, optionally substituted heteroaryl, optionally substituted heterocyclyl, urea, acyl, carboxy, alkoxycarbonyl, sulfanyl, sulfinyl and sulfonyl, e.g., diethylamino, methylsulfonylamino, furanyl-oxy-sulfonamino. Preferred substituents on an amino group include quinoxalinyl, acetyl or the amino group is unsubstituted.

Aryl and heteroaryl mean a 5- or 6-membered aromatic or heteroaromatic ring containing 0–4 heteroatoms selected from O, N, or S; a bicyclic 9- or 10-membered aromatic or heteroaromatic ring system containing 0–4 (or more) heteroatoms selected from O, N, or S; or a tricyclic 12- to 14-membered aromatic or heteroaromatic ring system containing 0–4 (or more) heteroatoms selected from O, N, or S. The aromatic 6- to 14-membered carbocyclic rings include those derived from, e.g., benzene, naphthalene, indane, tetralin, and fluorene and the 5- to 10-membered aromatic heterocyclic rings include those derived from, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylene and heteroarylene are similar to aryl and heteroaryl except that they are attached to the parent structure using two bonds.

Aralkyl refers to a residue in which an aryl moiety is attached to the parent structure via an alkyl residue. Examples include benzyl, phenethyl, phenylvinyl, phenylallyl and the like. Heteroaralkyl refers to a residue in which a heteroaryl moiety is attached to the parent structure via an alkyl residue. Examples include furanylmethyl, pyridylmethyl, pyrimidylethyl and the like.

Aralkoxy refers to the group —O-aralkyl. Similarly, heteroaralkoxy refers to the group —O-heteroaralkyl.

Halogen or halo refers to fluorine, chlorine, bromine or iodine. Fluorine, chlorine and bromine are preferred. Dihaloaryl, dihaloalkyl, trihaloaryl etC. refer to aryl and alkyl substituted with a plurality of halogens, but not necessarily a plurality of the same halogen; thus 4-chloro-3-fluorophenyl is within the scope of dihaloaryl.

Heterocycle means a cycloalkyl or aryl residue in which one to four of the carbons is replaced by a heteroatom such as oxygen, nitrogen or sulfur. Examples of heterocycles that fall within the scope of the invention include imidazoline, pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, piperidine, pyrimidine, thiophene, furan, oxazole, oxazoline, isoxazole, dioxane, tetrahydrofuran and the like. "N-heterocyclyl" refers to a nitrogen-containing heterocycle as a substituent residue. The term heterocyclyl encompasses heteroaryl, which is a subset of heterocyclyl. Examples of N-heterocyclyl residues include 4-morpholinyl, 4-thiomorpholinyl, 1-piperidinyl, 1-pyrrolidinyl, 3-thiazolidinyl, piperazinyl and 4-(3,4-dihydrobenzoxazinyl). Examples of substituted heterocyclyl include 4-methyl-1-piperazinyl and 4-benzyl-1-piperidinyl.

Linker refers to the distance imparted between portions of the molecule of the invention. L is a linker that places the $R_1$ moiety at a distance from the —$CH(R_2)$—CO—NH—Y moiety. Such a distance is preferably about 5–25 Å or 6–15 Å and more preferably about 7–12 Å or 8–10 Å.

Optional or optionally means that the subsequently described event or circumstance may or may not occur, and that the description includes instances where said event or circumstances occurs and instances in which it does not. For example, "optionally substituted alkyl" means either "alkyl" or "substituted alkyl" as defined herein. It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible and/or inherently unstable.

Substituted alkoxy refers to the group —O-(substituted alkyl). One preferred substituted alkoxy group is "polyalkoxy" or —O-(optionally substituted alkylene)-(optionally substituted alkoxy), and includes groups such as —$OCH_2CH_2OCH_3$, and glycol ethers such as polyethyleneglycol and —$O(CH_2CH_2O)_xCH_3$, where x is an integer of about 2–20, preferably about 2–10, and more preferably about 2–5. Another preferred substituted alkoxy group is hydroxyalkoxy or —$OCH_2(CH_2)_yOH$, where y is an integer of about 1–10, preferably about 1–4.

Substituted-alkyl, aryl, heteroaryl, aralkyl, heteroaralkyl and heterocyclyl refer respectively to alkyl, aryl, heteroaryl aralkyl, heteroaralkyl, and heterocyclyl wherein one or more (up to about 5, preferably up to about 3) hydrogen atoms are replaced by a substituent independently selected from the group: optionally substituted alkyl (e.g., fluoroalkyl), optionally substituted alkoxy, alkylenedioxy (e.g., methylenedioxy), optionally substituted amino (e.g., alkylamino, dialkylamino, arylamino, and heteroarylamino), optionally substituted amidino, optionally substituted aryl (e.g., phenyl), optionally substituted aralkyl (e.g., benzyl), optionally substituted aryloxy (e.g., phenoxy), optionally substituted aralkoxy (e.g., benzyloxy), carboxy (—COOH), carboalkoxy (i.e., acyloxy or —OOCR), carboxyalkyl (i.e., esters or —COOR), carboxamido, aminocarbonyl, benzyloxycarbonylamino (CBZ-amino), cyano, carbonyl, halogen, hydroxy, optionally substituted heteroaryl, optionally substituted heteroaralkyl, optionally substituted heteroaryloxy, optionally substituted heteroaralkoxy, nitro, sulfanyl, sulfinyl, sulfonyl, and thio.

Sulfanyl refers to the groups: —S-(optionally substituted alkyl), —S-(optionally substituted aryl), —S-(optionally substituted heteroaryl), and —S-(optionally substituted heterocyclyl).

Sulfinyl refers to the groups: —S(O)—H, —S(O)-(optionally substituted alkyl), —S(O)-optionally substituted aryl), —S(O)-(optionally substituted heteroaryl), and —S(O)-(optionally substituted heterocyclyl).

Sulfonyl refers to the groups: —$S(O_2)$—H, —$S(O_2)$-(optionally substituted alkyl), —$S(O_2)$-optionally substituted aryl), —$S(O_2)$-(optionally substituted heteroaryl), —S(O$_2$)-(optionally substituted heterocyclyl), —S(O$_2$)-(optionally substituted alkoxy), —S(O$_2$)-optionally substituted aryloxy), —S(O$_2$)-(optionally substituted heteroaryloxy), and —S(O$_2$)-(optionally substituted heterocyclyloxy).

Pharmaceutically acceptable acid addition salt refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Pharmaceutically acceptable base addition salts include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

Pharmaceutically acceptable esters refers to esters of compounds of the present invention which hydrolyze in vivo and include those that break down readily in the human body to leave the parent compound or a salt thereof. Examples of pharmaceutically acceptable, non-toxic esters of the present invention include $C_1$ to $C_6$ alkyl esters and $C_5$ to $C_7$ cycloalkyl esters, although $C_1$-to $C_4$ alkyl esters are preferred. Esters of the compounds of Formula I may be prepared according to conventional methods. Pharmaceutically acceptable, non-toxic esters of the present invention also include prodrug ester group, i.e., any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art. Other examples of prodrug ester groups can be found in the book "Pro-drugs as Novel Delivery Systems," by Higuchi and Stella., V. 14 of the A.C.S. Symposium Series.

Pharmaceutically acceptable amide refers to non-toxic amides of the present invention derived from ammonia, primary $C_1$ to $C_6$ alkyl amines and secondary $C_1$ to $C_6$ dialkyl amines. In the case of secondary amines, the amine may also be in the form of a 5- or 6-membered heterocycle containing one nitrogen atom. Amides derived from ammonia, $C_1$ to $C_3$ alkyl primary amides and $C_1$ to $C_3$ dialkyl secondary amides are preferred. Amides of the compounds of Formula I may be prepared according to conventional methods.

Pharmaceutically acceptable carrier is a medium that is used to prepare a desired dosage form of the inventive compound. A pharmaceutically acceptable carrier includes solvents, diluents, or other liquid vehicles; dispersion or suspension aids; surface active agents; isotonic agents; thickening or emulsifying agents; preservatives; solid binders; lubricants; and the like. *Remington's Pharmaceutical Sciences*, Fifteenth Edition, E. W. Martin (Mack Publishing Co., Easton, Pa. 1975) and *Handbook of Pharmaceutical Excipients*, Third Edition, A. H. Kibbe, ed. (*Amer. Pharmaceutical Assoc.* 2000), both of which are incorporated herein by reference in their entireties, disclose carriers used in formulating pharmaceutical compositions and known techniques for the preparation thereof.

Protecting group has the meaning conventionally associated with it in organic synthesis, i.e., a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, *Protective Groups in Organic Synthesis*, Third Edition, John Wiley & Sons, New York (1999), which is incorporated herein by reference in its entirety. For example, a hydroxy protected form of the inventive compounds are those where at least one of the hydroxyl groups is protected with a hydroxy protecting group. Likewise, keto groups in the inventive compounds and amines may similarly be protected.

Subject or patient refers to an animal, preferably a mammal, that has been the object of treatment, observation or experiment, and most preferably refers to a human whom has been the object of treatment and/or observation.

Therapeutically effective amount means that amount of active compound or pharmaceutical agent that elicits the biological or medicinal response in a tissue system, animal or human that is being sought by a research, veterinarian, medical doctor or other clinician, which includes alleviation of the symptoms of the disease or disorder being treated.

Many of the compounds described herein contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, including racemic mixtures, optically pure forms and intermediate mixtures. Optically active (R)— and (S)— isomers may be prepared using chiral synthons or chiral reagents, or resolved using conventional techniques.

Methods for the determination of stereochemistry and the separation of stereoisomers are well known to a person of ordinary skill in the art [see the discussion in Chapter 4 of J. March, *Advanced Organic Chemistry*, 4th ed., John Wiley and Sons, New York, N.Y., 1992]. When desired, the R—and S—isomers may be resolved by methods known to those skilled in the art, for example by formation of diastereoisomeric salts or complexes which may be separated, for example, by crystallisation; via formation of diastereoisomeric derivatives which may be separated, for example, by crystallisation, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where the desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting on enantiomer to the other by asymmetric transformation.

When the compounds described herein contain olefinic double bonds or other centers of geometric asymmetry, and unless specified otherwise, it is intended that the compounds include both E and Z geometric isomers. Likewise, all tautomeric forms are also intended to be included.

It should be understood that the compounds of this invention may exist in various equilibrium forms, depending on conditions including choice of solvent, pH, and others known to the practitioner skilled in the art. All such forms of these compounds are expressly included in the present invention. In particular, as the compounds of Formula I contain aldehyde and carboxylic acid groups, they may take a hemiacetal form as in Formula II as well as other acetal or hydrated forms.

Some of the crystalline forms for the compounds may exist as polymorphs and as such are included in the present invention. In addition, some of the compounds may form solvates with water (i.e., hydrates) or common organic solvents, and such solvates are also encompassed within the scope of this invention.

The present invention includes within its scope prodrugs of the compounds shown herein. In general, such prodrugs will be functional derivatives of the compounds that are readily convertible in vivo into the required compound. Thus, in the methods of treatment of the present invention, the term "administering" shall encompass the treatment of the various disorders described with the compounds specifically disclosed or with a compound which may not be specifically disclosed, but which converts to the specified compound in vivo after administration to a subject in need thereof. Conventional procedures for the selection and preparation of suitable prodrug derivatives are described, for example, in "Design of Prodrugs", H. Bundgaard ed., Elsevier, 1985. Protected forms of the inventive compounds are included within the scope of the present invention.

Implicit hydrogen atoms are omitted from the formulae for clarity, but should be understood to be present.

Compound of the Present Invention

The present invention is directed to a class of novel compounds that are inhibitors of caspase-1. By inhibiting or modulating the activity of caspase-1, but not other caspases, specific inhibition is accomplished. While not intending to be bound by any specific theory, the present invention capitalizes on the finding that perturbation of caspase-1 function reduces the production of IL-1 from prointerleukin-1 and/or the reduces the production of IGIF and frequently results in amelioration of disease states in which regulated cell death and the cytokine activity of IL-1 or IGIF play a role. The methods of inhibiting caspase-1 comprise contacting an inhibitor of the invention with caspase-1, particularly human caspase-1, including fragments and variants of caspase-1. In one embodiment the invention is diverted to human caspase-1 that is creptallized and which may be isolated from any inhibitor thereof.

Accordingly, the present invention relates to methods employing compounds represented by compounds of Formula I and in particular compounds represented by Formula II or Formula III:

Formula I

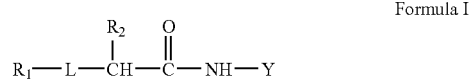

wherein:
R$_1$ is chosen from optionally substituted aryl, optionally substituted aralkyl, optionally substituted heteroaryl, and optionally substituted heteroaralkyl;

L is a linker;
R$_2$ is chosen from optionally substituted aryl, optionally substituted aralkyl, optionally substituted heteroaryl, and optionally substituted heteroaralkyl; and

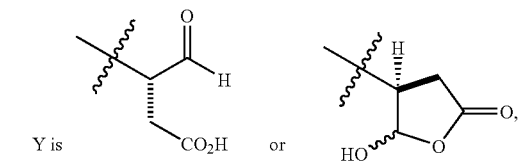

or single stereoisomers, mixtures of stereoisomers, or the pharmaceutically acceptable salts, amides, or esters thereof;

Formula II

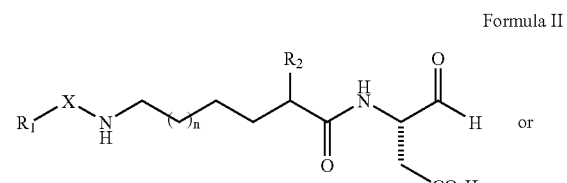

Formula III

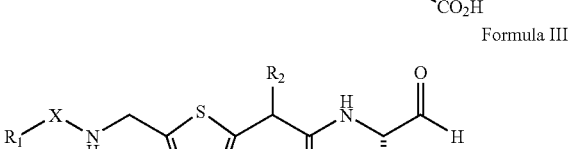

wherein:

R$_1$ is chosen from optionally substituted aryl, optionally substituted aralkyl, optionally substituted heteroaryl, and optionally substituted heteroaralkyl;
R$_2$ is chosen from optionally substituted aryl, optionally substituted aralkyl, optionally substituted heteroaryl, and optionally substituted heteroaralkyl;
X is —(CO)— or —(SO$_2$)—; and
n is 0 or 1;
including single stereoisomers, mixtures of stereoisomers, or pharmaceutically acceptable salts, esters, or amides thereof.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran, dimethylformamide, chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow.

However, other equivalent separation or isolation procedures can, of course, also be used.

Synthesis of the Compounds of Formula I and Formula II

The compounds of Formula I and Formula II are prepared by following the general procedures described in the Reaction Schemes below and as described in greater detail in the Examples.

Brief Description of Reaction Schemes

Reaction Scheme I illustrates a synthesis of compounds of Formula 106, an intermediate to compounds of Formula II.

Reaction Scheme 2 illustrates a synthesis of compounds of Formula 209 which are compounds of Formula II wherein X is —(CO)—.

Reaction Scheme 3 illustrates a synthesis of compounds of Formula 305 which are compounds of Formula II wherein X is —($SO_2$)—.

Reaction Scheme 4 illustrates another embodiment for a synthesis of compounds of Formula 209 which are compounds of Formula II wherein X is —(CO)—.

These schemes are merely illustrative of some methods by which the compounds of this invention can be synthesized, and various modifications to these schemes can be made and will be suggested to a person of ordinary skill in the art having regard to this disclosure. For example, although the methods shown utilize solid-phase synthesis techniques, one of ordinary skill in the art will appreciate that the compounds of the invention could be prepared using solution phase chemistries.

Starting Materials

The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser, *Reagents for Organic Synthesis*, vols. 1–17, John Wiley and Sons, New York, N.Y., 1991; Rodd, *Chemistry of Carbon Compounds*, vols. 1–5 and supplements, Elsevier Science Publishers, 1989; *Organic Reactions*, vols. 1–40, John Wiley and Sons, New York, N.Y., 1991; March, *Advanced Organic Chemistry*, 4th ed., John Wiley and Sons, New York, N.Y., 1992; and Larock, *Comprehensive Organic Transformations*, VCH Publishers, 1989. A synthesis resin of Formula 106 is prepared according to the procedure of PCT international Publication No. WO 00/23421, pages 37–40, using aminomethylated polystyrene (80 g, 0.85 mmol/g, NovaBiochem).

The starting materials, intermediates, and compounds of this invention may be isolated and purified using conventional techniques, including filtration, distillation, crystallization, chromatography, and the like. They may be characterized using conventional methods, including physical constants and spectral data.

Reaction Scheme 1

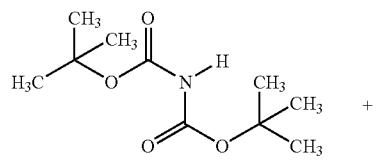

101

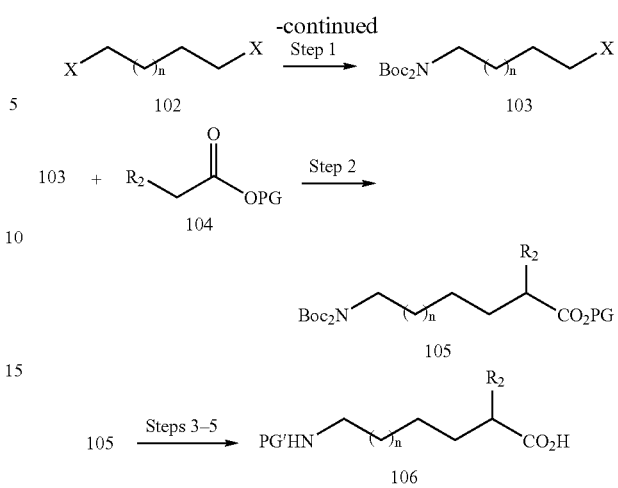

Preparation of Formula 103

Referring to Reaction Scheme 1, Step 1, to di-t-butyl iminodicarboxylate (the compound of Formula 101) dissolved in a polar, protic solvent (such as ethanol) is added about an equivalent of base (such as potassium hydroxide, preferably a solution of potassium hydroxide in a solvent such as ethanol), maintaining about room temperature. The resulting salt is isolated and purified. To the salt is added a suspension of about an equivalent of a dihaloalkane of Formula 102 wherein n is 0 or 1 (such as 1,4-dibromobutane) in a polar, aprotic solvent or mixture of solvents (such as dichloromethane/DMF). The reaction mixture is heated to about 50° C. and is stirred for from about 4 to about 12 hours. Completion of the reaction is monitored, e.g., by TLC. The product, a compound of Formula 103 is isolated and purified.

Preparation of Formula 105

Referring to Reaction Scheme 1, Step 2, in a separate flask containing an ester of Formula 104 (such as ethyl-2-thiopheneacetate) in a polar, aprotic solvent such as DMF is added portionwise a slight excess, preferably about 1.1 equivalents of sodium hydride, while maintaining the reaction temperature at about 0° C. The mixture is stirred for several minutes, and a solution of about an equivalent of the compound of Formula 103 in a polar aprotic solvent such as DMF is added. The reaction is warmed to room temperature, stirred for about 60 hours. The reaction is monitored for completion, e.g., by TLC. The product is isolated and purified to yield a compound of Formula 105.

Preparation of Formula 106

Referring to Reaction Scheme 1, Step 2, in a separate flask containing an ester of Formula 104 (such as ethyl-2-thiopheneacetate) in a polar, aprotic solvent such as DMF is added portionwise a slight excess, preferably about 1.1 equivalents of sodium hydride, while maintaining the reaction temperature at about 0° C. The mixture is stirred for several minutes, and a solution of about an equivalent of the compound of Formula 103 in a polar aprotic solvent such as DMF is added. The reaction is warmed to room temperature, stirred for about 60 hours. The reaction is monitored for completion, e.g., by TLC. The product is isolated and purified to yield a compound of Formula 105.

Referring to Reaction Scheme 1, Step 4, the acid is then dissolved in a polar, aprotic solvent such as dioxane in the presence of an aqueous acid, such as 4 M hydrochloric acid. The reaction is stirred for about an hour at room temperature. The reaction is monitored for removal of the Boc-protecting group, e.g., by TLC. The resulting free base is isolated.

Referring to Reaction Scheme 1, Step 5, the amine group is then protected with protecting group, PG', e.g., with an Fmoc group. More specifically, the resulting amino acid is dissolved in a polar, aprotic solvent or mixture of solvents such as 1:1 1,4-dioxane:water. To the solution is added a base, such as sodium bicarbonate, followed by Fmoc-OSu. The suspension is stirred overnight at room temperature. The product, a compound of Formula 106 is isolated and purified.

minutes, while maintaining the reaction at room temperature. Removal of the Fmoc-amine protecting group is monitored, e.g., by TLC. The resin is drained and washed with a polar, aprotic solvent such as DMF.

Referring to Reaction Scheme 2, Step 3, in a separate flask containing a compound of Formula 106 in a polar, aprotic solvent such as DMF is added an excess, preferably about 1.5 equivalents of PyBOP, followed by an excess of a base, preferably about 3 equivalents of diisopropylethylamine. The mixture is stirred at room temperature for several minutes and then added to the resin. The reaction is shaken overnight at room temperature, drained, and the resin is washed with a polar, aprotic solvent such as DMF to provide the support-bound compound of Formula 205.

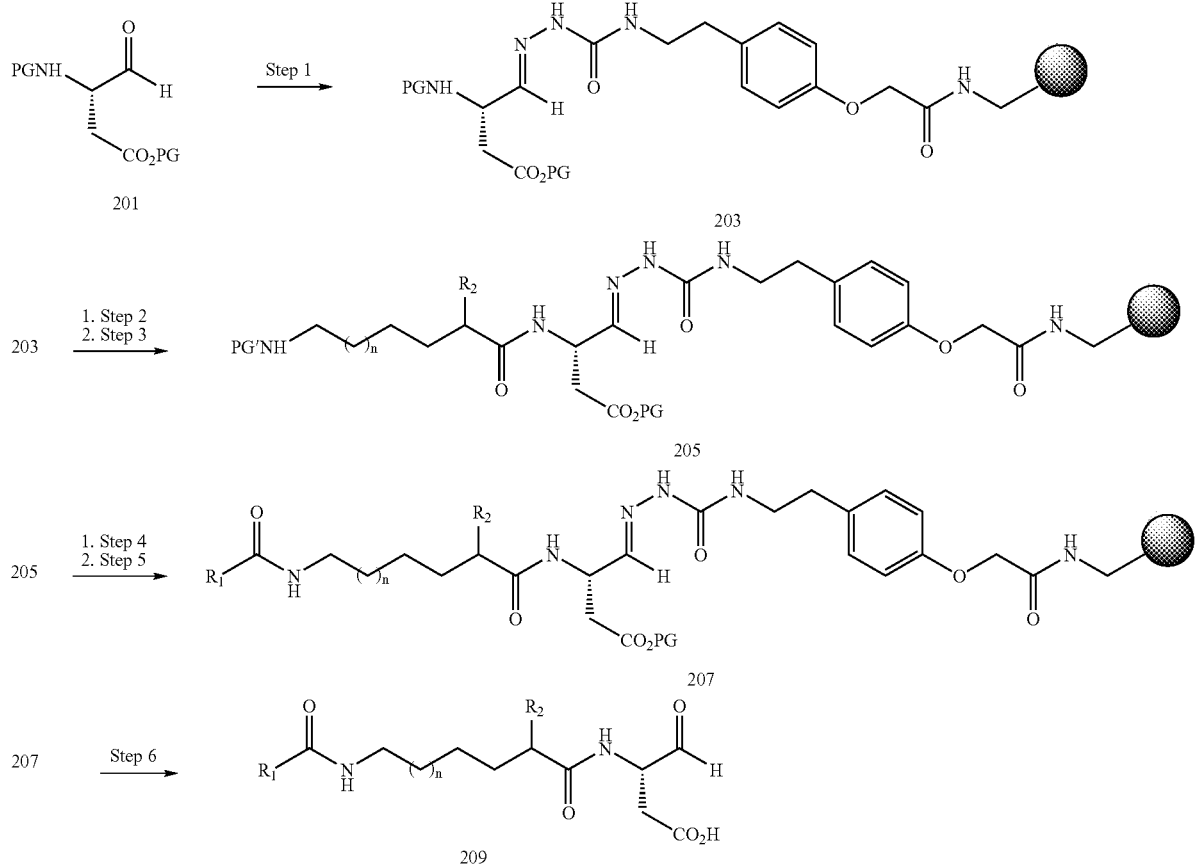

Preparation of Formula 203

Referring to Reaction Scheme 2, Step 1, a compound of Formula 201 is covalently linked to a suitable solid phase synthesis resin via a linker to yield, for example, a compound of Formula 203. Although one particular linker is illustrated, one of skill in the art will readily appreciate that others may be used.

Preparation of Formula 205

Referring to Reaction Scheme 2, Step 2, the amine protecting group of a compound of Formula 203 is then removed. For example, if the Fmoc group is used, then a compound of Formula 203 is treated with a base in a polar, aprotic solvent such as 20% piperidine in DMF for about 30

Preparation of Formula 207

Referring to Reaction Scheme 2, Step 4, the amine protecting group from a compound of Formula 205 is then removed. For example, if the Fmoc group is used to protect the amine, the support-bound compound of Formula 205 is treated with 20% piperidine in a polar, aprotic solvent such as DMF for about 30 min at room temperature. The resin is drained and washed.

Referring to Reaction Scheme 2, Step 5, in a separate vial containing an excess of an acid the formula $R_1CO_2H$ (or an activated version thereof) in a polar, aprotic solvent such as DMF is added an excess of a coupling reagent, such as PyBOP, followed by a base, such as diisopropylethylamine.

The activated acid solution is stirred for about 5 min at room temperature and added to the resin. The reaction is shaken overnight at room temperature, drained, and washed to provide a compound of Formula 207.

Preparation of Formula 209

Referring to Reaction Scheme 2, Step 6, the desired product is then removed from the synthesis resin. The product is isolated and purified to yield a compound of Formula 209, i.e., a compound of Formula II wherein X is —(CO)—.

-continued

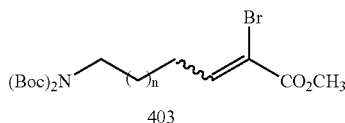

Reaction Scheme 3

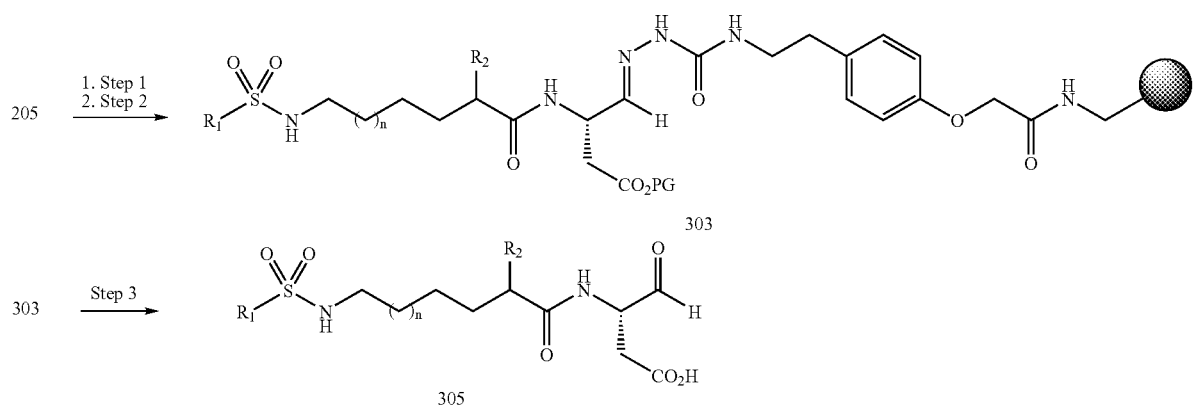

Preparation of Formula 303

Referring to Reaction Scheme 3, Step 1, the amine protecting group from a compound of Formula 205 is removed as described above with regard to Reaction Scheme 2, Step 4. For example, if the Fmoc group is used to protect the amine, the support-bound compound of Formula 205 is treated with 20% piperidine in a polar, aprotic solvent such as DMF for about 30 min at room temperature. The resin is drained and washed.

Referring to Reaction Scheme 3, Step 2, in a separate vial containing an excess of a sulfonyl chloride of the formula $R_1SO_2Cl$ in a polar, aprotic solvent such $CH_2Cl_2$ is added a base such as diisopropylethylamine. The solution is added to the resin and the reaction mixture is shaken overnight at room temperature. The resin is drained and washed to provide a compound of Formula 303.

Preparation of Formula 305

Referring to Reaction Scheme 3, Step 3, the desired product is then removed from the synthesis resin. The product is isolated and purified to yield a compound of Formula 305, i.e., a compound of Formula II wherein X is —($SO_2$)—.

Reaction Scheme 4

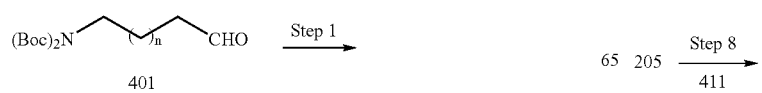

-continued

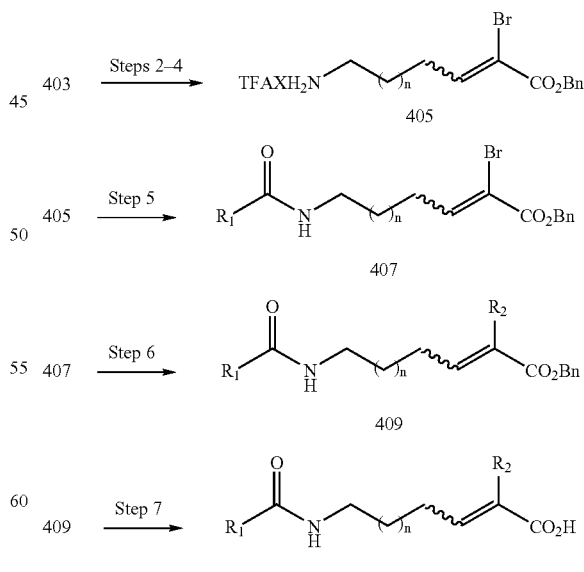

-continued

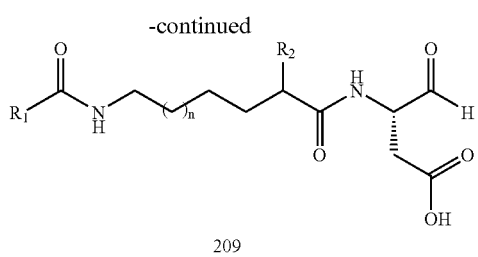

209

Preparation of Formula 403

Referring to Reaction Scheme 4, Step 1, to a suspension of sodium hydride (preferably, 60% sodium hydride in mineral oil) in a polar, aprotic solvent such as THF is added dropwise a solution of bromo-(dimethoxy-phosphoryl)-acetic acid methyl ester in a polar, aprotic solvent such as THF. The atmosphere is changed to nitrogen and after about 5 minutes at room temperature a solution of an aldehyde of Formula 401 in a polar, aprotic solvent such as THF is added dropwise. The reaction is monitored by TLC and LC/MS. The product, an ester of Formula 403, is isolated and purified.

Preparation of Formula 405

Referring to Reaction Scheme 4, Step 2, to an ester of Formula 403 in a polar, aprotic solvent such as THF is added aqueous base, preferably 1.0 M aqueous LiOH. The resulting mixture is stirred at room temperature until LC/MS indicatescomplete hydrolysis (~5–10 hour). The free acid is isolated and used without further purification.

Referring to Reaction Scheme 4, Step 3, to a mixture of the acid and an excess, preferably about 1.25 equivalents, of $Cs_2CO_3$ in a polar, aprotic solvent such as DMF is added an excess, preferably about 1.25 equivalents of benzyl bromide. After about 30 minutes LC/MS indicates complete conversion to the benzyl ester which is isolated and used without purification.

Referring to Reaction Scheme 4, Step 4, to a solution of the benzyl ester in a polar, aprotic solvent such as dichloromethane is added a strong acid such as TFA. After 20 minutes LC/MS indicates complete deprotection of the amine which is isolated as the salt and used without further purification.

Preparation of Formula 407

Referring to Reaction Scheme 4, Step 5, a mixture of about 1.5 equivalents of EDC, about 0.9 equivalents of HOBt, an excess of a base, such as diisopropylamine, and a carboxylic acid of the formula $R_1CO_2H$ in a polar, aprotic solvent such as dichloromethane is stirred at room temperature. After about 25 minutes, the temperature is lowered to 0° C. and a solution of amine of Formula 405 in a polar, aprotic solvent such as dichloromethane is added slowly. After 1 h at 0° C., the product, a compound of Formula 407 is isolated and purified.

Preparation of Formula 409

Referring to Reaction Scheme 4, Step 6, a mixture of a compound of Formula 407, an excess, preferably about two equivalents of a boronic acid of Formula $R_1$—$B(OH)_2$, about 0.5 equivalents of $Pd(dppf)Cl_2$ dichloromethane complex, and aqueous base, preferably about 1 M aqueous $K_2CO_3$, in a polar, aprotic solvent such as dioxane is heated reflux until LC/MS indicates complete conversion. The product, an ester of Formula 409, is isolated and used without further purification.

Preparation of Formula 411

Referring to Reaction Scheme 4, Step 7, to a suspension of a compound of Formula 409 and about 0.5 equivalents of Pd/C (preferably, Degussa type E101 NE/W, 10% Pd (dry basis) on activated carbon, wet) in a polar, protic solvent such as ethanol is added ammonium formate. The resulting mixture is heated at reflux until LC/MS indicated exhaustive reduction (usually ~0.5 h). After cooling to room temperature, the product, a compound of Formula 411 is isolated and used without further purification.

Preparation of Formula 209

Referring to Reaction Scheme 4, Step 8, the amine protecting group of a compound of Formula 205 is then removed as described above with regard to Reaction Scheme 2, Step 4. For example, if the Fmoc group is used, then a compound of Formula 205 is treated with a base in a polar, aprotic solvent such as 20% piperidine in DMF for about 30 minutes, while maintaining the reaction at room temperature. Removal of the Fmoc-amine protecting group is monitored, e.g., by TLC. The resin is drained and washed with a polar, aprotic solvent such as DMF.

In a separate flask containing a compound of Formula 411 in a polar, aprotic solvent such as DMF is added an excess, preferably about 1.5 equivalents of PyBOP, followed by an excess of a base, preferably about 3 equivalents of diisopropylethylamine. The mixture is stirred at room temperature for several minutes and then added to the resin. The reaction is shaken overnight at room temperature, drained, and the resin is washed with a polar, aprotic solvent such as DMF.

The desired product is then removed from the synthesis resin by treatment with. The product is isolated and purified to yield a compound of Formula 209, i.e., a compound of Formula II wherein X is —$(CO_2)$—.

Preferred Processes and Last Steps

A compound of Formula I is contacted with a pharmaceutically acceptable acid or base to form the corresponding acid or base addition salt.

A pharmaceutically acceptable acid addition salt of Formula I is contacted with a base to form the corresponding free base of Formula I.

A pharmaceutically acceptable base addition salt of Formula I is contacted with an acid to form the corresponding free acid of Formula I.

A compound of Formula I is esterified to give the corresponding compound having a carboxylic acid ester.

A compound of Formula I is contacted with an optionally substituted amine under conditions suitable for production of the corresponding amide.

A compound of Formula I is contacted with an alcohol to yield an acetal or hemiacetal.

A compound of Formula I is contacted with an acid to yield a hemiacetal.

A racemic mixture of isomers of a compound of Formula I is placed on a chromatography column and separated into (R)— and (S)— enantiomers.

Compounds prepared by the above-described process of the invention and the products incorporating them (e.g., pharmaceutical formulations) can be identified by the presence of a detectable amount of certain novel starting materials and/or reactants. While it is well known that pharmaceuticals must meet pharmacopoeia standards before approval and/or marketing, and that synthetic reagents (such as LiOH or potassium hydroxide) or side products should not exceed the limits prescribed by pharmacopoeia standards, final compounds prepared by a process of the present invention may have minor, but detectable, amounts of such materials present, for example, at levels in the range of 95% purity with no single impurity greater than 1%. These levels can be detected, e.g., by emission spectroscopy. It is important to monitor the purity of pharmaceutical compounds for the presence of such materials, which presence is additionally disclosed as a method of detecting use of a process of the invention.

The present invention provides a novel composition of matter or pharmaceutical formulation including a compound or pharmaceutically acceptable salt of Formula I and a detectable amount of one or more of the following:

a compound of Formula 102;

a compound of Formula 201, or the corresponding compound wherein the protecting group, PG, has been removed;

a compound of Formula 201, or the corresponding compound wherein the protecting groups, i.e., Boc groups, have been removed; and/or a lithium or potassium reagent employed in the synthesis thereof.

Preferred Compounds

When considering the compounds of Formula II and Formula III in a preferred embodiment, X is —(CO)—. In another preferred embodiment, X is —($SO_2$)—. More preferably, n is 1.

Preferred linkers (L) of the invention place the $R_1$ moiety at a distance from the —CH($R_2$)—CO—NH—Y moiety of from about 5–25 Å and more preferably 6–15 Å and even more preferably 7–12 Å or 8–10 Å.

Preferred linkers include —Z—$(CH_2)_m$—Ar—$(CH_2)_n$— wherein Z is —C(=O)NH—, —NHC(=O)—, or —$SO_2$NH—; m and n are each 0, 1, 2, or 3; and Ar is a 5 or 6 membered arylene or heteroarylene. In one embodiment, Ar is a 5 membered heteroarylene. Illustrative examples include furanylene, imidazolylene, oxazolylene, pyranylene, thienylene, and thiazolylene. In another embodiment, Ar is a 6 membered arylene or heteroarylene. Illustrative examples include phenylene, pyridylene, and pyrimidylene. One preferred linker is —Z—$CH_2$-thienylene and more preferably —C(=O)NH—$CH_2$-thienylene-.

Other suitable linkers include but are not limited to:
—$(CH_2)_m$—O—$(CH_2)_n$—; —$(CH_2)_m$—NR—$(CH_2)_n$—; —$(CH_2)_m$—NRCONR—$(CH_2)_n$—; $(CH2)_m$—NR-COO—$(CH_2)_n$—; —$(CH_2)_m$—CONR—$(CH_2)_n$—; —$(CH_2)_m$—NRCO—$(CH_2)_n$—; —$(CH_2)_m$—NRSO$_2$—$(CH_2)_n$—; —$(CH_2)_m$—CO—$(CH_2)_n$—; —$(CH_2)_m$—NRCONRSO$_2$—$(CH_2)_n$—; —$(CH_2)_m$—NRCONRCO—$(CH_2)_n$—; —$(CH_2)_m$—SO$_2$—$(CH_2)_n$—; —$(CH_2)_m$—SO$_2$CH$_2$CO—$(CH_2)_n$—; —$(CH_2)_m$—SO$_2$NR—$(CH_2)_n$— and, —$(CH_2)_m$—SCH$_2$CO—$(CH_2)_n$— where m and n are each 0, 1, 2, 3, 4 or 5 and wherein R is each independently hydrogen, $C_1$–$C_5$ alkyl, $C_1$–$C_5$ hydroxyalkyl, or $C_1$–$C_5$ alkylhalide. Moreover, the hydrogens of each methylene unit in the linker can be independently replaced with a suitable group such as a hydroxy, halide, or methyl.

Particularly preferred linkers include but are not limited to:
—$(CH_2)_m$—CONR—$(CH_2)_n$—; —$(CH_2)_m$—NRCO—$(CH_2)_n$—; —$(CH_2)_n$—; and —$(CH_2)_m$—SO$_2$NR—$(CH_2)_n$— wherein m and n are each 0, 1, 2, 3, 4, or 5, more preferably where m is 0, 1, or 2 and n is 3, 4, or 5, and preferably were R is hydrogen. For example, —SO$_2$NH(CH$_2$)$_4$—, —CONH—(CH$_2$)$_4$—, and —CONH—(CH$_2$)$_5$—.

Alkenylene or alkynylene linkers, i.e., alkylene linkers that contain one or more double or triple bonds may also be used as linkers. For example, ethenylene, ethynylene, propenylene, propynylene, butenylene and butynylene may be used. Such linkers may also contain one or more heteroatoms. Alkenylene or alkynylene linkers may also form a linker with Z, described above.

Preferred linkers also include 5-6 membered carbocyclic linkers that may contain one or more, preferably 1 or 2 heteroatoms such as O, N or S, such as a thienylene group. Other examples of 5-6 membered carbocyclic groups that may contain a heteroatom include arylene, i.e., -(aryl)- such as phenylene, furylene, thienylene, pyranylene, pyrrolylene, irridiazolylene, pyrozolylene, thiazolylene, oxazolylene, pyridylene, pyrazinylene, pyrimidinylene, or pyridazinylene. Carbocyclic linkers may also form a linker with alkenylene and/or alkynylene and/or Z, described above.

In addition a carbocyclic linker may be cycloalkylene, i.e., —$C_5H_8$— or —$C_6H_{10}$— or that may contain one or two points of unsaturation and that may contain a heteroatom instead of a backbone carbon, such as cyclopentylene, cyclohexylene, pyrrolidinylene, pyrrolinylene, imidazolinylene, imidazol idinylene, pirazolidinylene, pirazolinylene, piperidylene, piperazinylene, or morpholinylene. Cycloalkylene linkers may also form a linker with Z and/or alkylene, alkenylene and/or alkynylene linkers, described above.

More preferably, $R_1$ is optionally substituted aryl or optionally substituted heteroaryl. Yet more preferably, $R_1$ is chosen from optionally substituted phenyl, optionally substituted naphthyl, optionally substituted pyridyl, optionally substituted quinolinyl, optionally substituted thienyl, optionally substituted oxazolyl, optionally substituted 2,3-dihydrobenzo[b]thien-2-yl, optionally substituted quinoxalinyl, optionally substituted tetrahydroisoquinolinyl, optionally substituted benzoxazolyl, and optionally substituted quinoxalinylamino. Preferably $R_1$ is dimethylphenyl, tolyl methyl, quinoxalinyl, tolyl cyclopentyl, morpholinylpyridyl, napthalenyl, chloro benzo[b]thienyl, amino dichlorophenyl, quinolinyl, phenyloxazolyl, tolyl, thienyl, trifluoro ace tyl tetrahydro isoquinolinyl, pyridyl thienyl, fluro chloro carboxy phenyl, hydroxy carboxy phenyl, benzooxazolyl, or quinoxalinyl amino phenyl.

In a preferred embodiment, $R_2$ is chosen from H, optionally substituted thienyl, optionally substituted phenyl, optionally substituted pyridyl, and optionally substituted benzofuranyl. Preferably, $R_2$ is selected from the group of H, thienyl, preferably 2-thienyl, alkyl thienyl, preferably 3-methyl 2-thienyl, phenoxy, preferably 4-phenoxy, phenyl, alkylphenyl, preferably 4-isopropyl phenyl, acetylaminophenyl, preferably 4-acetylaminophenyl, pyridyl, preferably 3-pyridyl, and benzooxazole.

Preferred optional substituents include alkyl, preferably methyl and isopropyl; alkoxy, preferably carboxy; amino, preferably amino, quinoxalinylamino, or acetylamino amino; aryl, preferably phenyl, tolyl, or pyridyl; halo, preferably chloro or fluro; hydroxy; morpholinyl trifluoromethyloxo and NHAc. Particularly preferred substituents with respect to $R_1$ is methyl, carboxy, amino, quinoxalinyl amino, phenyl, tolyl, pyridyl, chloro, fluoro, hydroxy, morpholino and trifluoroacetyl, or no substituent. Particularly preferred substituents with respect to $R_2$ are methyl, isopropyl, hydroxy and NHAc, or no substituent.

Particularly preferred compounds of Formula II and Formula III include those defined in the Examples

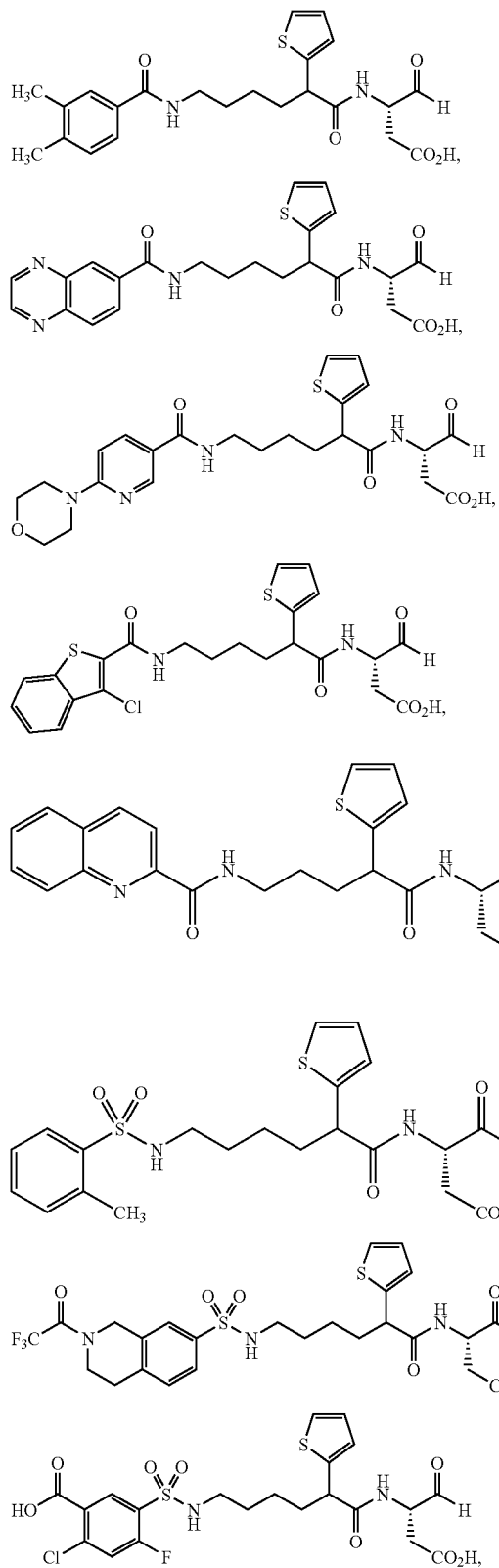
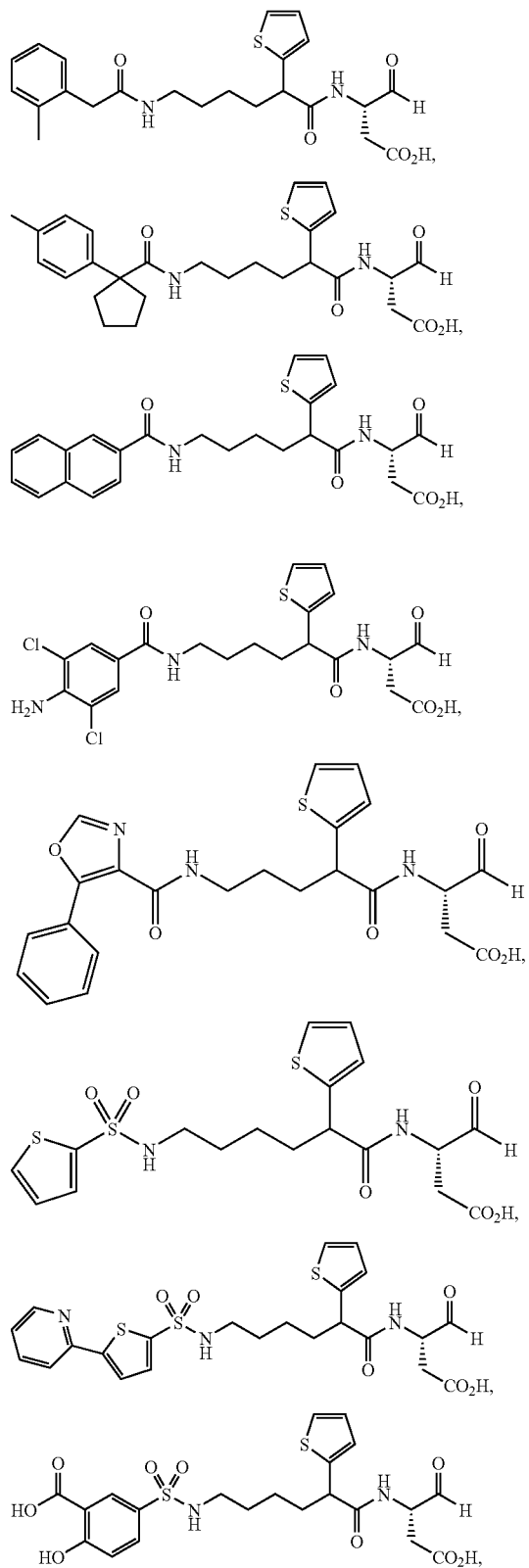

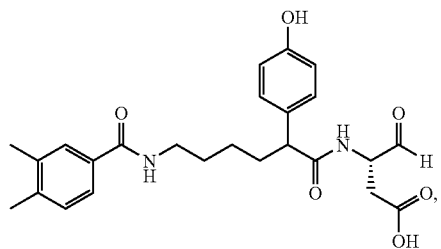
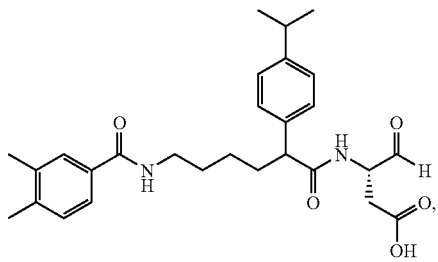
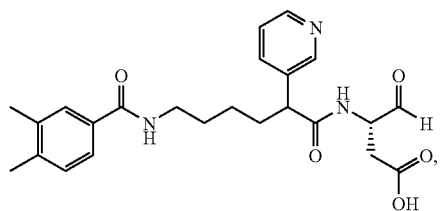
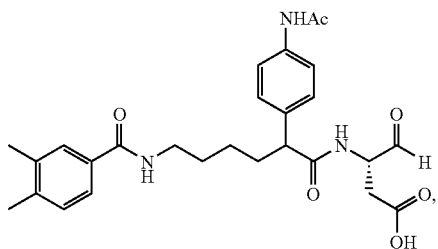
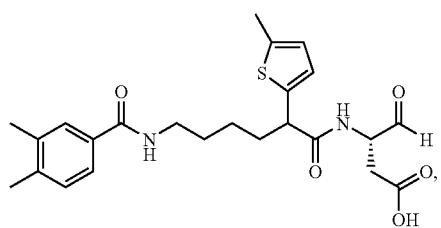
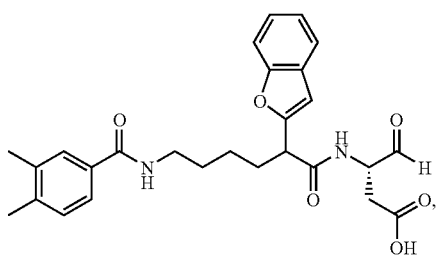
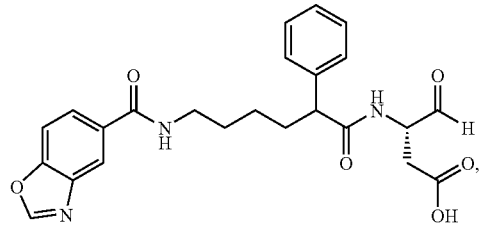
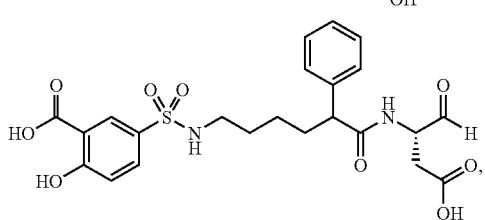
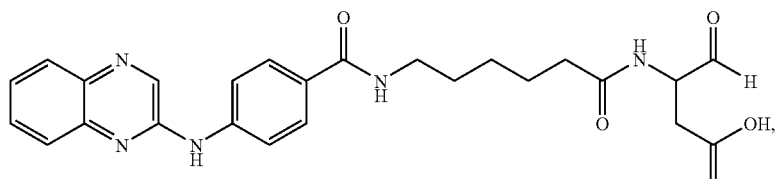
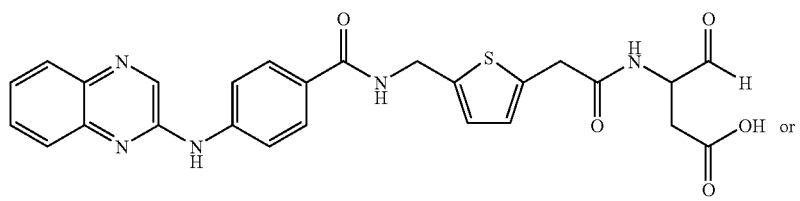
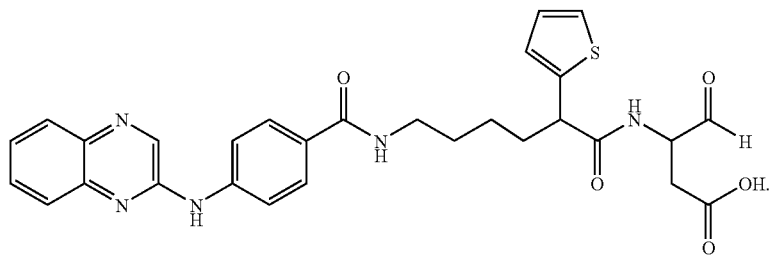

Utility, Testing and Administration

The compositions of the invention find use in a variety of applications. The compositions of the present invention can be used to reduce or prevent cell death in the nervous system (brain, spinal cord, and peripheral nervous system) under various conditions of ischemia and excitotoxicity, including, but not limited to, focal ischemia due to stroke and global ischemia due to cardiac arrest, as well as spinal cord injury (Emery et al., *J. Neurosurgery* 89:911–920 (1998)). One particular usage is to treat the effects of oxygen deprivation which can occur during the birth of infants in high-risk labors or drowning. The compositions can also be used to reduce or prevent cell death in the nervous system due to traumatic injury (such as head trauma), viral infection or radiation-induced nerve cell death (for example, as a side-effect of cancer radiotherapy), as well as acute bacterial meningitis (Braun et al., *Nat. Med* 5:298–302 (1999)). The compositions can also be used to reduce or prevent cell death in a range of neurodegenerative disorders, including but not limited to Alzheimer's disease (Mattson et al., *Brain Res.* 807:167–176 (1998)), Huntington's Disease, Parkinson's Disease, multiple sclerosis, amyotrophic lateral sclerosis, and spinobulbar atrophy. The in vivo neuroprotective properties of compositions of the invention can be tested in a rat transient focal brain ischemia model (Xue et al., *Stroke* 21:166 (1990)). The cell death inhibitors may also be used to treat or ameliorate cell death in acute bacterial meningitis (Braun et al., *Nat. Med.* 5:298–302 (1999)).

The compositions of the invention can be used to reduce or prevent cell death in any condition which potentially results in the death of cardiac muscle (Black et al., *J. Mol. Cel. Card.* 30:733–742 (1998) and Maulik et al., *Free Radic. Biol. Med.* 24:869–875 (1998)). This includes myocardial infarction due to myocardial ischemia and reperfusion, congestive heart failure and cardiomyopathy. One particular application is to reduce or prevent myocardial cell death as occurs in certain viral infections of the heart.

The in vivo activity of the compositions of the invention can be tested using the "mouse liver apoptosis" model described by Rodriguez et al. (*J. Exp. Med.* 184:2067–2072 (1996)). In this model, mice are treated intravenously (IV) with an antiFas antibody which induces massive apoptosis in the liver and other organs, leading to generalized organ failure and death. This model is useful for indirectly testing the systemic bioavailability of the compositions of the invention, as well as their in vivo anti-apoptotic properties. The compositions of the invention therefore can be used to reduce or prevent apoptosis of liver cells (Jones et al., *Hepatology* 27:1632–42 (1998)) such as in sepsis (Jaeschke et al., *J. Immunol.* 160:3480–3486 (1998)) and hereditary tyrosinemia type 1 (HT1) (Kubo et al., *Prov. Natl. Acad. Sci. USA* 95:9552–9557 (1998)). The compositions of the invention also can be used to treat hepatitis (Suzuki, *Proc. Soc. Exp. Biol. Med.* 217:450–454 (1998)).

The compositions of the invention can be used to reduce or prevent cell death of retinal neurons (Kermer et al., *J. Neurosci.* 18:4656–4662 (1998) and Miller et al., *Am. J. Vet. Res.* 59:149–152 (1998)) as can occur in disorders which increase intraocular pressure (such as glaucoma) or retinal disorders associated with the aging process (such as age-related macular degeneration). The inhibitors can also be used to treat hereditary degenerative disorders of the retina, such as retinitis pigmentosa.

The compositions of the invention can also be used to reduce or prevent cell death in the kidney. This includes renal amyloidosis (Hiraoka et al., *Nippon Jinzo Gakkai Shi.* 40:276–83 (1998)), acute renal failure (Lieberthal et al., *Semin. Nephrol.* 18:505–518 (1998)), murine tubular epithelial cell death induced by cyclosporine A (Ortiz et al., *Kidney International Supp.* 68:S25–S29 (1998)) and HIV-induced nephropathy (Conaldi et al., *J. Clin. Invest.* 102: 2041–2049 (1998)).

The compositions of the invention can also be used to reduce or prevent cell death of buccal mucosa due to chronic alcohol ingestion (Slomiany et al., *Biochem. Mol. Biol. Int.* 45:1199–1209 (1998)).

The compositions of the invention can also be used to reduce or prevent cell death in plants (Richberg et al., *Curr. Opin. Plant Biol.* 1:480–485 (1998)), such as plant cell death due to pathogens (Pozo et al., *Curr. Biol.* 8:1129–1132 (1998) and Greenberg et al., *Cell* 77:551–563 (1994)).

The compositions of the invention can also be used to reduce or prevent cell death due to radiation and ultraviolet-irradiation (Sheikh et al., *Oncogene* 17:2555–2563 (1998)).

The compositions of the invention can also be used to reduce or prevent apoptotic death of bone marrow cells in myelodysplastic syndromes (MDS) (Mundle et al., *Am. J. Hematol.* 60:36–47 (1999)).

The compositions of the invention can also be used to reduce or prevent premature death of cells of the immune system, and are particularly useful in treating immune deficiency disorders, such as acquired immune deficiency syndrome (AIDS), severe combined immune deficiency syndrome (SCIDS) and related diseases. The compositions can also be used to treat radiation-induced immune suppression.

Transplantation of human organs and tissues is a common treatment for organ failure. However, during the transplantation process, the donor organ or tissue is at risk for cell death since it is deprived of its normal blood supply prior to being implanted in the host. This ischemic state can be treated with compositions of the invention by infusion into the donor organ or tissue, or by direct addition of the compositions to the organ/tissue storage medium. For example, it was reported that treatment of the embryonic nigral cell suspension with Ac-YVAD-cmk, a caspase-1 inhibitor, mitigated DNA fragmentation and reduced apoptosis in transplants. It also increased survival of dopaminergic neurons grafted to hemiparkinsonian rats, and thereby substantially improved functional recovery (Schierle et al., *Nat. Med.* 5:97–100 (1999)). Compositions of the invention may also be used to reduce or prevent cell death in the donor organ/tissue after it has been transplanted to protect it from the effects of reperfusion injury and/or effects of host immune cells which kill their targets by triggering apoptosis.

The cytoprotective effects of compositions of the invention can also be used to prevent the death of human or animal sperm and eggs used in in vitro fertilization procedures. These inhibitors can be used during the harvesting process and can also be included in the storage medium.

Mammalian cell lines, insect cells and yeast cells are commonly used to produce large amounts of recombinant proteins (such as antibodies, enzymes or hormones) for industrial or medicinal use. The lifespan of some of these cell lines is limited due to growth conditions, the nature of the recombinant molecule being expressed (some are toxic) and other unknown factors. The lifespans of industrial cell lines can be extended by including these compositions of the invention in the growth medium in a concentration range of 1–100 µM.

The factors governing hair growth and loss are largely unknown. There is some evidence, however, that hair follicle regression (referred to as catagen) may be due at least partially to apoptosis. Therefore, it is contemplated that the compositions of the present invention can be used to treat hair loss that occurs due to various conditions, including but not limited to male-pattern baldness, radiation-induced or chemotherapy-induced hair loss, and hair loss due to emotional stress. There is also evidence that apoptosis may play a role in the loss of hair color. Therefore, it is contemplated that the compositions of the present invention can also be used in treating or preventing cases of premature graying of the hair.

The death of skin epithelial cells can occur after exposure to high levels of radiation, heat or chemicals. It is contemplated that the compositions of the present invention can be used to treat, reduce or prevent this type of skin damage. In one particular application, the compositions can be applied as part of a topical formulation, e.g., an ointment, to treat acute over-exposure to the sun and to prevent blistering and peeling of the skin.

The invention relates to a method of treating, ameliorating or preventing oral mucositis, gastrointestinal mucositis, bladder mucositis, proctitis, bone marrow cell death, skin cell death and hair loss resulting from chemotherapy or radiation therapy of cancer in an animal, comprising administering to the animal in need thereof an effective amount of a composition of the present invention.

When animals are treated with chemotherapeutic agents and/or radiation to kill cancer cells, an unwanted side effect is the apoptotic death of rapidly dividing non-cancer cells. Such non-cancer cells include cells of the gastrointestinal tract, skin, hair, and bone marrow cells. According to the present invention, caspase inhibitors are administered to such non-cancer cells to prevent apoptosis of such cells. In a preferred embodiment, the caspase inhibitors are administered locally, e.g., to the gastrointestinal tract, mouth, skin or scalp to prevent apoptosis of the gastrointestinal, mouth, skin or hair cells but allowing for the death of the cancer cells. Thus, in one example, it is possible to treat brain cancer with chemotherapy or radiation therapy and protect the outer skin, hair cells, gastrointestinal tract and bone marrow by local administration of a caspase inhibitor. In the case of oral mucositis, the caspase inhibitor can be applied, for example, in the form of a mouth wash or mouth rinse, in a gel, or in the form of an oral slow release lozenge to prevent activation of caspases and apoptotic cell death induced by the chemotherapeutic agent or by radiation. In the case of gastrointestinal mucositis, the caspase inhibitor can be applied in a form such that it is not absorbed systemically or in a form that coats the surface of the gastrointestinal tract, or a suppository formulation for the treatment of gastrointestinal mucositis. In the case of proctitis, the capsase inhibitor may be applied as part of an enema or suppository. In the case of bladder mucositis, the caspase inhibitor may be applied though a bladder catheter. For prevention of radiation or chemotherapy-induced hair loss, the caspase inhibitor can be applied, for example, to the scalp in the form of a hair rinse, hair gel, shampoo or hair conditioner. Importantly, the caspase inhibitor can be applied prior to the administration of the chemotherapeutic agent or radiation, thus preventing the onset of the damaging effects of the chemotherapeutic agent or radiation to the normal cells.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g., humans, orally at a dose of 0.0025 to 50 mg/kg, or an equivalent amount of the pharmaceutically acceptable salt thereof, per day of the body weight of the mammal being treated for apoptosis-mediated disorders, e.g., neuronal cell death, heart disease, retinal disorders, polycystic kidney disease, immune system disorders and sepsis. Preferably, about 0.01 to about 10 mg/kg is orally administered to treat or prevent such disorders. For intramuscular injection, the dose is generally about one-half of the oral dose. For example, for treatment or prevention of neuronal cell death, a suitable intramuscular dose would be about 0.0025 to about 25 mg/kg, and most preferably, from about 0.01 to about 5 mg/kg.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In a topical formulation, the compound may be present at a concentration of about 0.01 to 100 mg per gram of carrier. In a preferred embodiment, the compound is present at a concentration of about 0.07–1.0 mg/ml, more preferably, about 0.1–0.5 mg/ml, most preferably, about 0.4 mg/ml.

Accordingly, the compositions of the invention are administered to cells. By "administered" herein is meant administration of a therapeutically effective dose of the mitotic agents of the invention to a cell either in cell culture or in a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. By "cells" herein is meant almost any cell in which mitosis or meiosis can be altered.

A "patient" for the purposes of the present invention includes both humans and other animals, particularly mammals, and other organisms. Thus the methods are applicable to both human therapy and veterinary applications. In the preferred embodiment the patient is a mammal, and in the most preferred embodiment the patient is human.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally or topically and which can be used for the preferred type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by injection, topically or orally, contain from about 0.01 to 99 percent, preferably from about 0.25 to 75 percent of active compound(s), together with the excipient.

Moreover, the compounds of the invention can be combined with other active agents, such as those that are used to treat inflammation, rheumatoid arthritis, and sepsis.

The pharmaceutical compositions of the invention may be administered to any animal which may experience the beneficial effects of the compounds of the invention. Foremost among such animals are mammals, e.g., humans, although the invention is not intended to be so limited.

The caspase inhibitors and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired. In general, the caspase inhibitors are administered locally to the tissues that are to be protected from apoptosis and separately from the chemotherapeutic agent. For example, cisplatin may be administered by i.v. injection to treat a cancer such as brain, lung, breast, liver, kidney, pancreatic, ovarian, prostatic cancer, and the caspase inhibitor administered locally to treat, ameliorate, or prevent apototic cell death in the mouth or gastrointestinal tract, such as a mouth wash for the treatment of oral mucositis; and i.v. injectable aqueous solution for the treatment of bone marrow cell death; and an oral formulation suitable for coating the gastrointestinal surfaces or an enema or suppository formulation for the treatment of gastrointestinal mucositis including proctitis. The caspase inhibitors may also be applied through a bladder catheter for the treatment, amelioration or prevention of bladder mucositis. Alternatively or concurrently, the caspase inhibitors may be applied topically to the skin and/or scalp to treat, ameliorate or prevent apoptotic cell death of hair and skin cells. In a further embodiment, the chemotherapeutic agent or radiation may be applied locally to treat a localized cancer such as brain, lung, breast, liver, kidney, pancreatic, ovarian, prostatic cancer, and the caspase inhibitor administered systemically, e.g., by i.v. injection, to treat, ameliorate or prevent apoptotic cell death of the gastrointestinal tract cells, mouth epithelial cells, bone marrow cells, skin cells and hair cells. In the case of oral mucositis in brain cancer treatment, for example, a caspase inhibitor that does not penetrate the blood-brain barrier can be applied, for example, systemically by i.v. injection followed by irradiation of the brain tumor. This would protect the oral mucosa from the harmful effects of radiation but the caspase inhibitor would not protect the brain tumor from the therapeutic effects of radiation. Importantly, the caspase inhibitor can be applied prior to administration of the radiation, thus preventing the onset of the damaging effects of the radiation to the normal mucosa cells.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, enemas or suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension include, for example, sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin damage, such as that caused by exposure to high levels of radiation, including ultraviolet radiation, heat or chemicals.

One or more additional substances which have therapeutic effects on the skin may also be incorporated in the compositions. Thus, the composition may also contain one or more compounds capable of increasing cyclic-AMP levels in the skin. Suitable compounds include adenosine or a nucleic acid hydrolysate in an amount of about 0.1–1% and papaverine, in an amount of about 0.5–5%, both by weight based on the weight of the composition. Also suitable are β-adrenergic agonists such as isoproterenol, in an amount of about 0.1–2% or cyclic-AMP, in an amount of about 0.1–1%, again both by weight based on the weight of the composition. Other suitable types of additional active ingredients which may be incorporated in the compositions of this invention include any compounds known to have a beneficial effect on skin. Such compounds include retinoids such as Vitamin A, in an amount of about 0.003–0.3% by weight and chromanols such as Vitamin E or a derivative thereof in an amount of about 0.1–10% by weight, both based on the weight of the composition. Additionally, anti-inflammatory agents and keratoplastic agents may be incorporated in the cosmetic composition. A typical anti-inflammatory agent is a corticosteroid such as hydrocortisone or its acetate in an amount of about 0.25–5% by weight, or a corticosteroid such as dexamethasone in an amount of about 0.025–0.5% by weight, both based on the weight of the composition. A typical keratoplastic agent is coal tar in an amount of about 0.1–20% or anthralin in an amount of about 0.05–2% by weight, both based on the weight of the composition.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the active ingredient, in a suitable high molecular weight alcohol such as propylene glycol or polyethylene glycol.

In addition, these compositions may include other medicinal agents, growth factors, wound sealants, carriers, etc., that are known or apparent to those skilled in the art. The compositions of the invention are administered to a warm-blooded animal, such as human, already suffering from a skin damage, such as a burn, in an amount sufficient to allow the healing process to proceed more quickly than if the host were not treated. Amounts effective for this use will depend on the severity of the skin damage and the general state of health of the patient being treated. Maintenance dosages over a prolonged period of time may be adjusted as necessary. For veterinary uses, higher levels may be administered as necessary.

In the case of an animal suffering from decreased hair growth, the compositions of the invention are administered in an amount sufficient to increase the rate of hair growth. Amounts effective for this use will depend on the extent of decreased hair growth, and the general state of health of the patient being treated. Maintenance dosages over a prolonged period of time may be adjusted as necessary. For veterinary uses, higher levels may be administered as necessary.

When the compounds are to be administered to plants, they may be applied to the leaves and/or stems and/or flowers of the plant, e.g., by spraying. The compounds may be spayed in particulate form or dissolved or suspended in an appropriate carrier, e.g., in water or an oil water emulsion.

The compounds may also be combined with the soil of the plant. In this embodiment, the compounds are taken up by the roots of the plant.

In a preferred embodiment, the caspase inhibitor is formulated as part of a mouthwash for the treatment, amelioration or prevention of oral mucositis. Such mouthwashes are aqueous solutions of the caspase inhibitor which may also contain alcohol, glycerin, synthetic sweeteners and surface-active, flavoring and coloring agents. They may also contain anti-infective agents such as hexetidine and cetylpyridinium chloride. The mouthwashes may also contain topical anesthetics (e.g., benzocaine, cocaine, dyclonine hydrochloride, lidocaine, proparacaine hydrochloride or teracaine hydrochloride), for example, for relieving pain of radiation or chemotherapy-induced sores. The mouth washes may have either acidic or basic pH. See Remington's Pharmaceutical Sciences, A. R. Gennaro (ed.), Mack Publishing Company, pp. 1045, 1046, 1526 and 1965 (1990).

In another preferred embodiment, the caspase inhibitor is formulated as an oral formulation which is capable of coating the gastrointestinal surfaces for the treatment, amelioration or prevention of gastrointestinal mucositis. Examples of gastrointestinal mucositis include esophageal mucositis, gastric mucositis, and intestinal mucositis. Such formulations may comprise gastric antacids such as aluminum carbonate, aluminum hydroxide gel, bismuth subnitrate, bismuth subsalicylate, calcium carbonate, dihydroxyaluminum sodium carbonate, magaldrate, magnesium carbonate, magnesium hydroxide, magnesium oxide, sodium bicarbonate, milk of bismuth, dihydroxyaluminum aminoacetate, magnesium phosphate, magnesium trisilicate and mixtures thereof. Other additives include without limitation $H_2$-receptor antagonists, digestants, anti-emetics, adsorbants, and miscellaneous agents. See Remington's Pharmaceutical Sciences, A. R. Gennaro (ed.), Mack Publishing Company, pp. 774–778 (1990).

Chemotherapy agents such as cisplatin and radiation therapy often induce early and late onset emesis in the patient. Thus, in one embodiment an antiemetic is coadministered together with the caspase inhibitor to avoid emesis and retain contact of the caspase inhibitor with the gastrointestinal tract. Examples of such antiemetics include without limitation compounds that block the dopaminergic emetic receptors such as metoclopramide and trimethobenzamide, and cannabinoids. Metoclopramide may be administered orally prior to and/or during chemotherapy/radiation therapy/caspase inhibitor therapy to prevent the early emesis response and then later by intranasal administration according to U.S. Pat. Nos. 5,760,086 and 4,536,386 to prevent delayed onset emesis. During the period after chemotherapy/radiation therapy, both the caspase inhibitor and the antiemetic may be coadministered to treat, ameliorate or prevent gastrointestinal mucositis.

In a further embodiment, the caspase inhibitor may be formulated as an i.v. injectable solution for the treatment, amelioration or prevention of bone marrow cell death.

The compositions of the invention may be administered to a warm-blooded animal, such as human, already suffering from chemotherapy or radiation therapy-induced non-cancer cell death, or, more preferably, before or during therapy with chemotherapy or radiation.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

Example 1

Synthesis of 3-[6-(3,4-dimethyl-benzoylamino)-2-thien-2-yl-hexanoylamino]-4-oxo-butyric acid a) To di-t-butyl-iminodicarboxylate (50 g, 230 mmol) was added KOH (12.9 g, 230 mmol) in ethanol (100 mL). After stirring for 1 h at room temperature, diethyl ether was added (2×200 mL) and the resulting white precipitate was filtered, washed with diethyl ether (2×100 mL) and dried over $Na_2SO_4$. To the potassium salt as a suspension in dichloromethane/DMF (600 mL, 4:1) was added 1,4-dibromobutane (22.2 mL, 219 mL). The reaction was stirred overnight at 50° C. and the resulting mixture was filtered and washed with dichloromethane (3×150 mL). The filtrate was concentrated under reduced pressure; the residue was dissolved in EtOAc (500 mL) and washed with brine (250 mL). The organic layer was dried over $Na_2SO_4$ and concentrated under reduced pressure to give a clear oil. The crude residue was

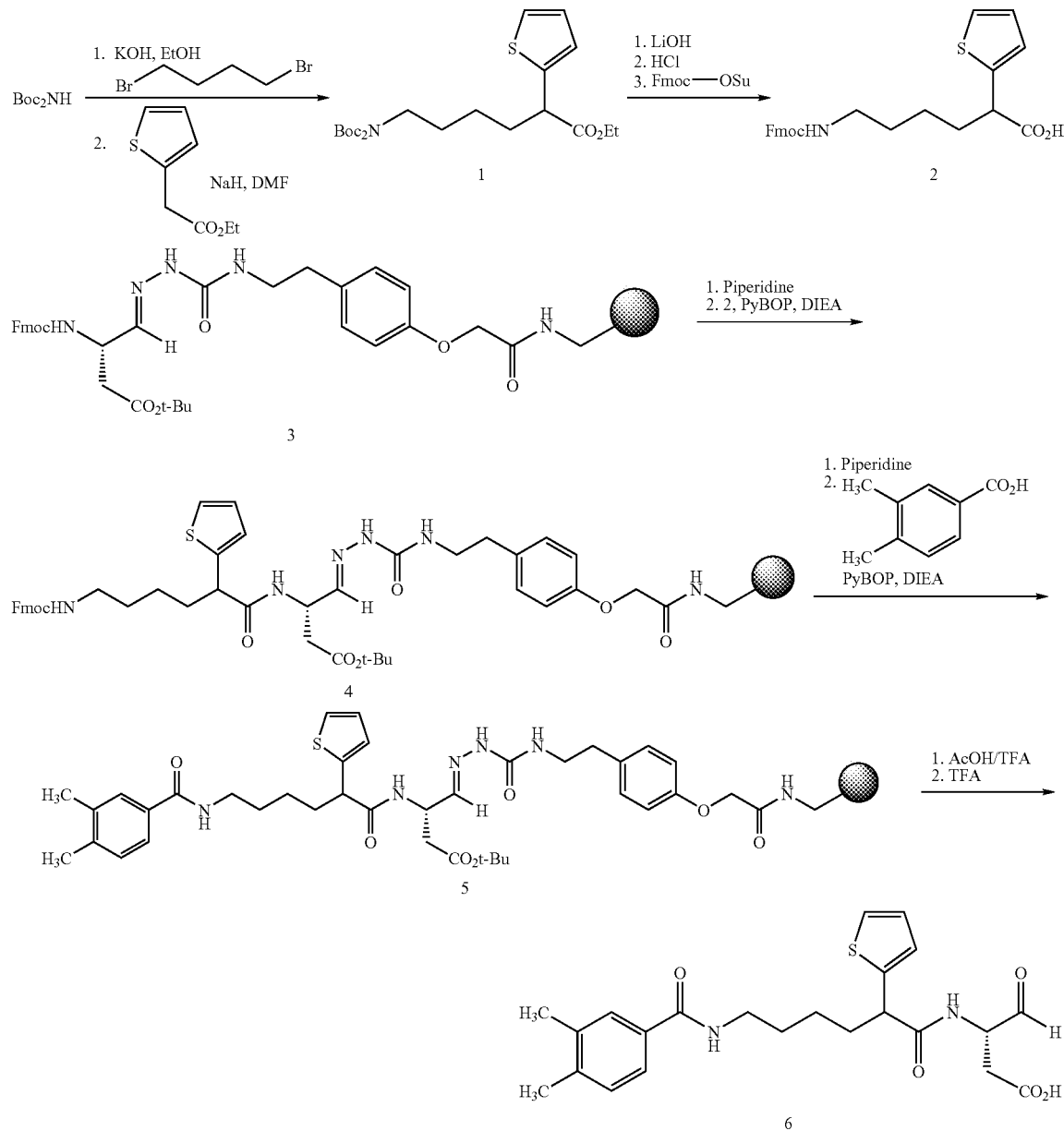

purified by flash chromatography (SiO$_2$: 5% ethyl acetate in hexanes) to afford 52 g (65%) of the desired bromide.

In a separate flask containing ethyl-2-thiopheneacetate (22.3 mL, 148 mmol) in DMF (500 mL) at 0° C. was added portionwise sodium hydride (6.5 g, 163 mmol, 60% in mineral oil). The mixture was stirred for 10 min, and the butyl bromide was added (52 g, 148 mmol, in 100 ml DMF). The reaction was warmed to room temperature, stirred for 60 h, quenched with 1 M HCl (200 mL), and extracted with EtOAc (3×400 mL). The combined organic layer was washed with brine (1×400 mL), dried over Na$_2$SO$_4$, and concentrated under reduced pressure to give a black oil. The crude product was purified by flash chromatography (SiO$_2$: 10 to 50% ethyl acetate in hexanes) to give 1 (45 g, 70%). ES (+) MS m/e=464 (M+23).

b) To 1 (45 g) in a solution of methanol and water (400 mL, 3:1) was added LiOH (5 g, 209 mmol). The reaction was stirred 1 h at room temperature then acidified using 1 M HCl (200 mL). The mixture was extracted with EtOAc (3×400 mL); the combined organic extracts were dried over Na$_2$SO$_4$ and concentrated under reduced pressure to provide the free acid (42 g).

The acid was dissolved in dioxane (100 mL) and HCl (100 mL, 4 M in 1,4-dioxane) was added. After stirring for 1 h at room temperature, the solvent was removed under reduced pressure.

The resulting amino acid was dissolved in a solution of 1,4-dioxane and water (500 mL, 1:1). Sodium bicarbonate (42.8 g, 510 mmol) was added, followed by Fmoc-OSu (37.8 g, 112 mmol). The tan suspension was stirred overnight at room temperature. The mixture was acidified using a 10% aqueous solution of citric acid and extracted with EtOAc (3×300 mL). The combined organic extracts were dried over Na$_2$SO$_4$ and concentrated under reduced pressure to give a crude yellow oil (66 g). The crude material was purified by flash chromatography (SiO$_2$: 2% AcOH in 4:1 ethyl acetate/hexanes) to provide 2 (37.8 g, 85% over 3 steps). ES (+) MS m/e=458 (M+23).

c) Resin 3 was prepared according to the procedure of PCT international Publication No. WO 00/23421, pages 37–40, using aminomethylated polystyrene (80 g, 0.85 mmol/g, NovaBiochem). The theoretical loading of resin 3 was approximately 0.4 mmol/g and this loading level was used for all subsequent calculations. Resin 3 (35 g, ~14 mmol) was treated with 20% piperidine in DMF (200 mL) for 30 min at room temperature. The resin was drained and washed with DMF (10×200 mL). In a separate flask containing 2 (12.3 g, 28.2 mmol) in DMF (200 mL) was added PyBOP (22.0 g, 42.3 mmol) followed by diisopropylethylamine (14.7 mL, 84.6 mmol). The mixture was stirred at room temperature for 5 min and then added to the resin. The reaction was shaken overnight at room temperature, drained, and the resin was washed with DMF (10×200 mL) to provide the support-bound intermediate 4.

d) Resin 4 (300 mg, 0.12 mmol) was treated with 20% piperidine in DMF (5 mL) for 30 min at room temperature. The resin was drained and washed with DMF (10×5 mL). In a separate vial containing 3,4-dimethylbenzoic acid (75 mg, 0.48 mmol) in DMF (4 mL) was added PyBOP (375 mg, 0.72 mmol) followed by diisopropylethylamine (251 µL, 1.44 mmol). The activated acid solution was stirred for 5 min at room temperature and added to the resin. The reaction was shaken overnight at room temperature, drained, and washed with DMF (5×5 mL) followed by CH$_2$Cl$_2$ (5×5 mL) to provide 5.

e) Resin 5 was treated with THF/AcOH/acetaldehyde/TFA (4 mL, 5:1:1:0.25), shaken at room temperature for 3 h, and then filtered and washed with CH$_2$Cl$_2$ (2×4 mL). The combined filtrate was concentrated to dryness under reduced pressure. The resulting crude residue was treated with TFA/CH$_2$Cl$_2$ (3 mL, 1:1). The solution was stirred at room temperature for 1 h and the solvent was removed under reduced pressure. The crude residue was purified by reverse-phase HPLC to yield 6. ES (+) MS m/e=445 (M+H).

Example 2

Synthesis of 4-oxo-3-[2-thien-2-yl-6-(2-o-tolyl-acetylamino)-hexanoylamino]-butyric acid

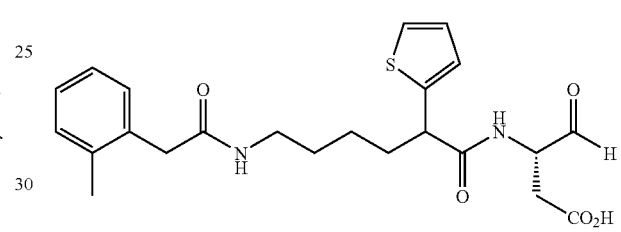

7

The title compound 7 was prepared according to the procedure of Example 1d–e except for using 2-methylphenylacetic acid as a reagent instead of 3,4-dimethylbenzoic acid. ES (+) MS m/e=445 (M+H).

Example 3

Synthesis of 4-oxo-3-{6-[(quinoxaline-6-carbonyl)-amino]-2-thien-2-yl-hexanoylamino}-butyric acid

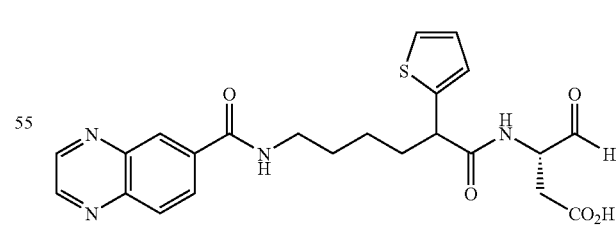

8

The title compound 8 was prepared according to the procedure of Example 1d–e except for using quinoxaline-6-carboxylic acid as a reagent instead of 3,4-dimethylbenzoic acid. ES (+) MS m/e=469 (M+H).

Example 4

Synthesis of 4-oxo-3-{2-thien-2-yl-6-[(1-p-tolyl-cyclopentanecarbonyl)-amino]-hexanoylamino}-butyric acid

9

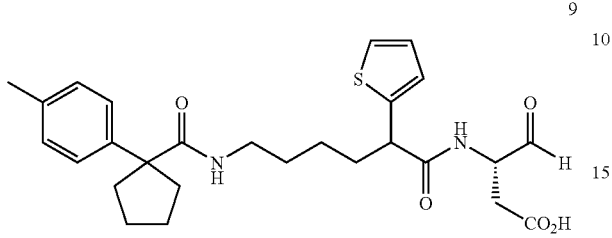

The title compound 9 was prepared according to the procedure of Example 1d–e except for using 1-(p-tolyl)-1-cyclopentanecarboxylic acid as a reagent instead of 3,4-dimethylbenzoic acid. ES (+) MS m/e=499 (M+H).

Example 5

Synthesis of 3-{6-[(6-morpholin-4-yl-pyridine-3-carbonyl)-amino]-2-thien-2-yl-hexanoylamino}-4-oxo-butyric acid

10

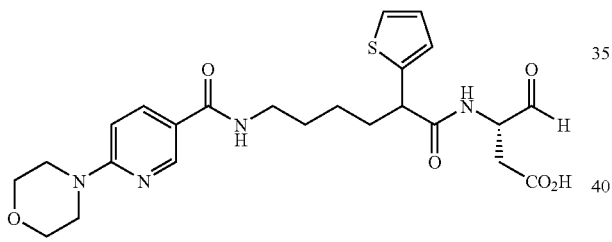

The title compound 10 was prepared according to the procedure of Example 1d–e except for using 6-morpholinonicotinic acid as a reagent instead of 3,4-dimethylbenzoic acid. ES (+) MS m/e 503 (M+H).

Example 6

Synthesis of 3-{6-[(naphthalene-2-carbonyl)-amino]-2-thien-2-yl-hexanoylamino}-4-oxo-butyric acid

11

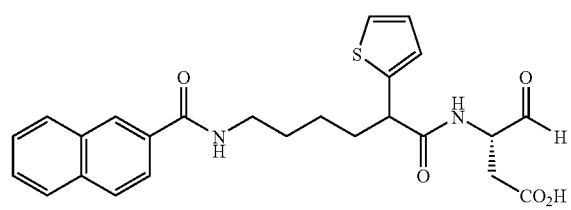

The title compound 11 was prepared according to the procedure of Example 1d–e except for using 2-napthoic acid as a reagent instead of 3,4-dimethylbenzoic acid. ES (+) MS m/e=467 (M+H).

Example 7

Synthesis of 3-{6-[(3-chloro-benzo[b]thiophene-2-carbonyl)-amino]-2-thien-2-yl-hexanoylamino}-4-oxo-butyric acid

12

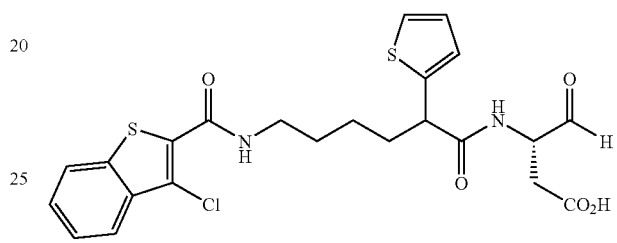

The title compound 12 was prepared according to the procedure of Example 1d–e except for using 3-Chloro-benzothiophene-2-carboxylic acid as a reagent instead of 3,4-dimethylbenzoic acid. ES (+) MS m/e=507 (M+H).

Example 8

Synthesis of 3-[6-(4-amino-3,5-dichloro-benzoylamino)-2-thien-2-yl-hexanoylamino]-4-oxo-butyric acid

13

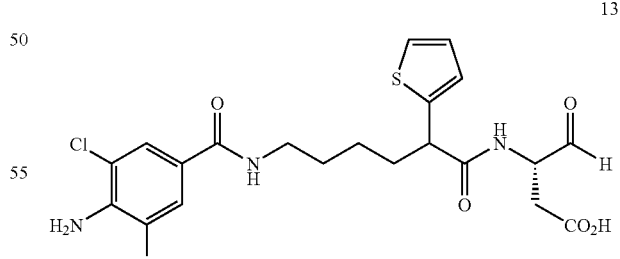

The title compound 13 was prepared according to the procedure of Example 1d–e except for using 4-amino-3,5-dichloro benzoic acid as a reagent instead of 3,4-dimethylbenzoic acid. ES (+) MS m/e=500 (M+H).

Example 9

Synthesis of 4-oxo-3-{5-[(quinoline-2-carbonyl)-amino]-2-thien-2-yl-pentanoylamino}-butyric acid

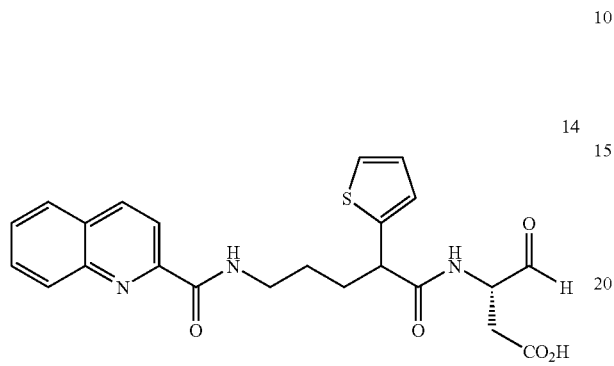

14

The title compound 14 was prepared according to the procedure of Example 1a–e except for using 1,3-dibromopropane as a reagent instead of 1,4-dibromobutane and quinoline-2-carboxylic acid as a reagent instead of 3,4-dimethylbenzoic acid. ES (+) MS m/e=454 (M+H).

Example 10

Synthesis of 4-oxo-3-{5-[(5-phenyl-oxazole-4-carbonyl)-amino]-2-thien-2-yl-pentanoylamino}-butyric acid

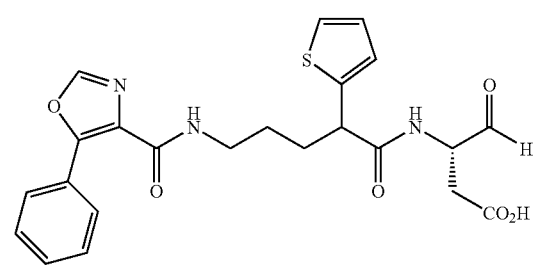

15

The title compound 15 was prepared according to the procedure of Example 1a–e except for using 1,3-dibromopropane as a reagent instead of 1,4-dibromobutane and 5-phenyl-oxazole-4-carboxylic acid as a reagent instead of 3,4-dimethylbenzoic acid. ES (+) MS m/e 470 (M+H).

Example 11

Synthesis of 4-oxo-3-[2-thien-2-yl-6-(toluene-2-sulfonylamino)-hexanoylamino]-butyric acid

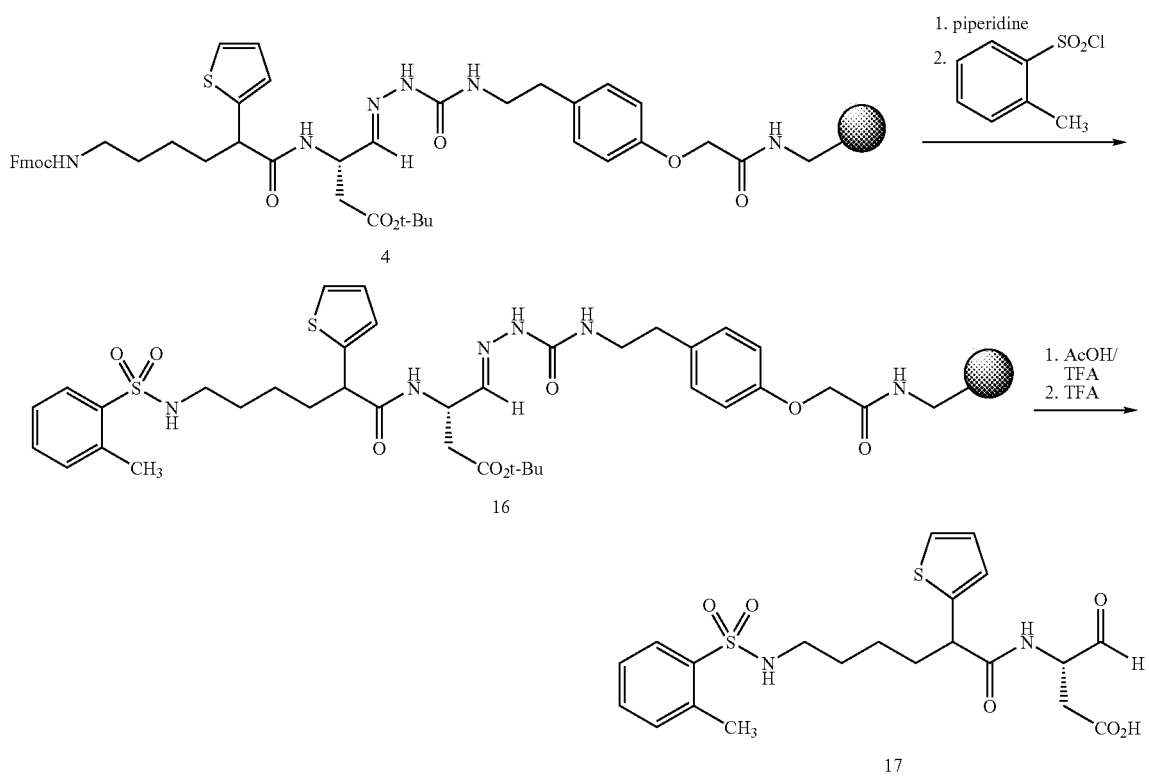

a) Resin 4 (300 mg, 0.12 mmol) was treated with 20% piperidine in DMF (5 mL) for 30 min at room temperature. The resin was drained followed by washing with DMF (5×5 mL) and CH$_2$Cl$_2$ (5×5 mL). In a separate vial containing o-tolylsulfonyl chloride (143 mg, 0.75 mmol) in CH$_2$Cl$_2$ (4 mL) was added diisopropylethylamine (261 μL, 1.5 mmol). The solution was added to the resin and the reaction mixture was shaken overnight at room temperature. The resin was drained and washed with CH$_2$Cl$_2$ (10×5 mL) to provide 16.

b) The title compound 17 was prepared according to Example 1e except for using 16 instead of 5. ES (+) MS m/e=467 (M+H).

Example 12

Synthesis of 4-oxo-3-[6-(thiophene-2-sulfonylamino)-2-thien-2-yl-hexanoylamino]-butyric acid

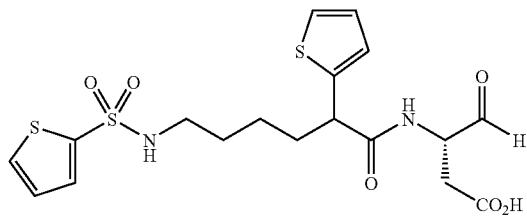

18

The title compound 18 was prepared according to the procedure of Example 11a,b except for using 2-thiophenesulfonyl chloride as a reagent instead of o-tolylsulfonyl chloride. ES (+) MS m/e=459 (M+H).

Example 13

Synthesis of 4-oxo-3-{2-thien-2-yl-6-[2-(2,2,2-trifluoro-acetyl)-1,2,3,4-tetrahydro-isoquinoline-7-sulfonylamino]-hexanoylamino}-butyric acid

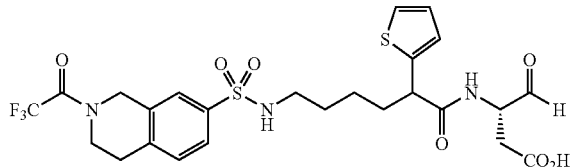

19

The title compound 19 was prepared according to the procedure of Example 11a,b except for using 1,2,3,4-tetrahydro-2-(trifluoroacetyl)-isoquinoline-7-sulfonyl chloride as a reagent instead of o-tolylsulfonyl chloride. ES (+) MS m/e=604 (M+H).

Example 14

Synthesis of 4-oxo-3-[6-(5-pyrid-2-yl-thiophene-2-sulfonylamino)-2-thien-2-yl-hexanoylamino]-butyric acid

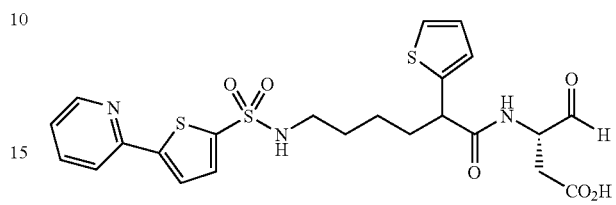

20

The title compound 20 was prepared according to the procedure of Example 11a,b except for using 2-(2-pyridine)-thiophene-5-sulfonyl chloride as a reagent instead of o-tolylsulfonyl chloride. ES (+) MS m/e=535 (M+H).

Example 15

Synthesis of 5-[5-(2-carboxy-1-formyl-ethylcarbamoyl)-5-thien-2-yl-pentylsulfamoyl]-2-chloro-4-fluoro-benzoic acid

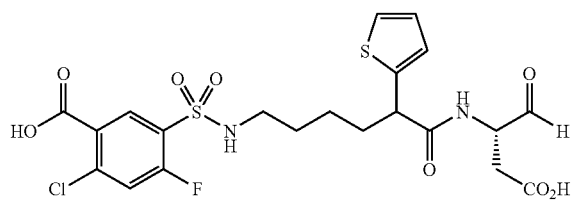

21

The title compound 21 was prepared according to the procedure of Example 11a,b except for using 2-chloro-5-chlorosulfonyl-4-fluorobenzoic acid as a reagent instead of o-tolylsulfonyl chloride. ES (+) MS m/e=549 (M+H).

Example 16

Synthesis of 5-[5-(2-carboxy-1-formyl-ethylcarbamoyl)-5-thien-2-yl-pentylsulfamoyl]-2-hydroxy-benzoic acid

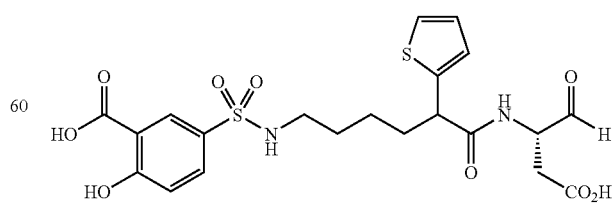

22

The title compound 22 was prepared according to the procedure of Example 11a,b except for using 5-chlorosul-

Example 17

Synthesis of 3-[6-(3,4-dimethyl-benzoylamino)-2-(4-hydroxy-phenyl)-hexanoylamino]-4-oxo-butyric acid

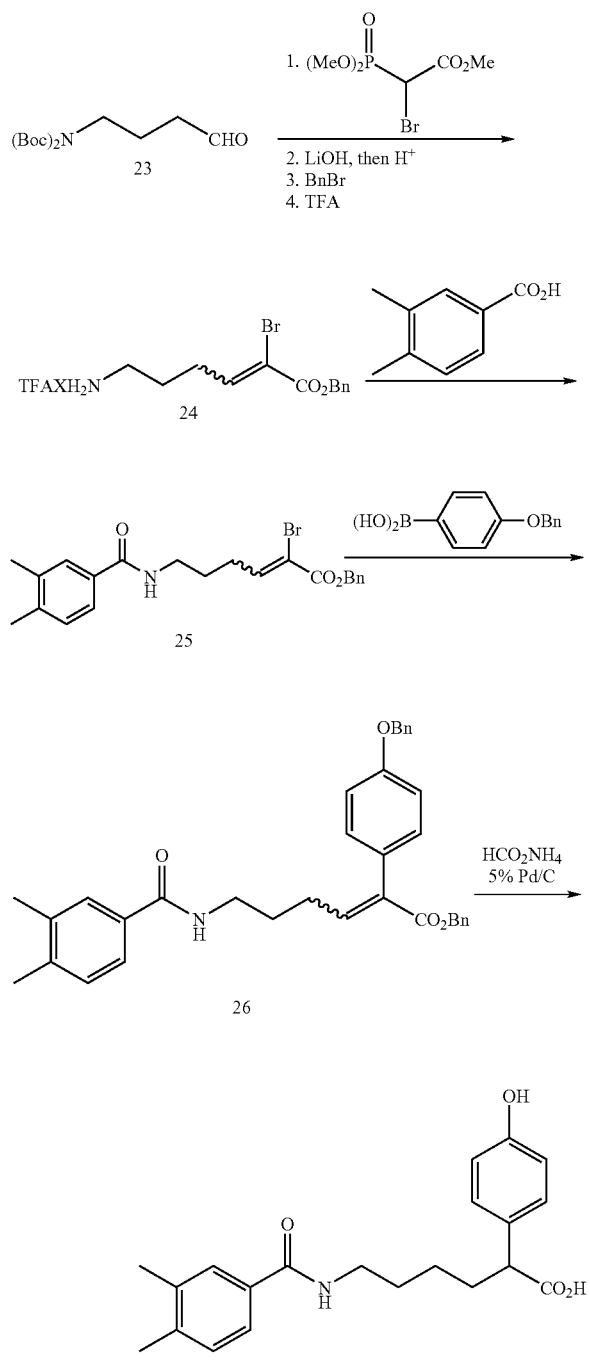

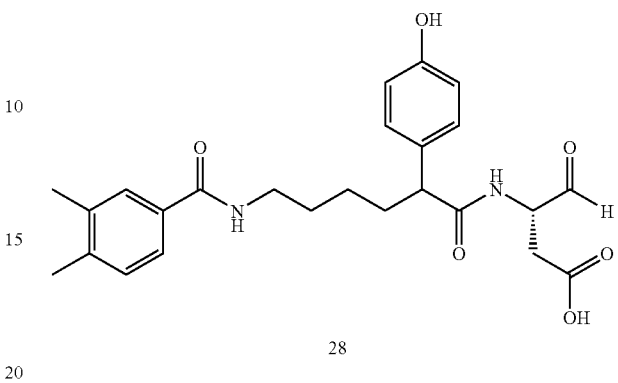

a) To a suspension of sodium hydride (153 mg, 3.82 mmol, 60% in mineral oil) in THF (15 mL) was added dropwise a solution of bromo-(dimethoxy-phosphoryl)-acetic acid methyl ester (1.09 g, 4.18 mmol) in THF (5 mL). The atmosphere was changed to nitrogen and after 5 minutes at room temperature a solution of the aldehyde 23[1] in THF (5 mL) was added dropwise. The reaction was monitored by TLC and LC/MS; when the aldehyde had been consumed, the mixture was diluted with diethyl ether and washed with aqueous saturated ammonium chloride. The aqueous layer was extracted with diethyl ether and the combined organic phases were dried ($Na_2SO_4$) and concentrated. The crude residue was purified by flash column chromatography ($SiO_2$: gradient 0 to 8% ethyl acetate in hexane) to yield 1.07 g (69%, ~1:1 mixture of diastereomers by NMR) as a viscous oil. ES (+) MS m/e=446 (M+Na+).

[1] Carretero, J. C.; Arrayas, R. G. *J. Org. Chem.*, 1998,63, 2993–3005.

To the ester (689 mg, 1.63 mmol) in THF (3.0 mL) was added 1.0 M aqueous LiOH (2.04 mL, 2.04 mmol). The resulting mixture was stirred at room temperature until LC/MS indicated complete hydrolysis (~5–10 h). To the solution was added water and the pH was adjusted to 3–4 with 1 M citric acid. The mixture was extracted with ethyl acetate and the organic layer was dried ($Na_2SO_4$) and concentrated to yield 642 mg (97%) of a white solid. ES (+) MS m/e=431 (M+Na+).

To a mixture of the acid (973 mg, 2.40 mmol) and $Cs_2CO_3$ (977 mg, 3.00 mmol) in DMF (8.0 mL) was added benzyl bromide (286 µL, 2.40 mmol). After 30 minutes LC/MS indicated complete conversion to the benzyl ester. The reaction mixture was diluted with ethyl acetate/hexanes (2:3) and washed with water and brine. The organic layer was dried ($Na_2SO_4$) and concentrated to yield 1.08 g (90%) of a white solid. ES (+) MS m/e=520 (M+Na+).

To a solution of the ester (5.00 g, 10.0 mmol) in dichloromethane (20 mL) was added TFA (40 mL). After 20 minutes LC/MS indicated complete deprotection of the amine and the solvent was removed under reduced pressure. The crude oil was co-evaporated with dichloroethane (3×). Residue 24 was then dried under high vacuum and used without further purification. ES (+) MS m/e=298 (M+1).

b) A mixture of EDC (3.07 g, 16.0 mmol), HOBt (1.53 g, 10.0 mmol), diisopropylamine (4.53 mL, 2.60 mmol), and 3,4-dimethylbenzoic acid (1.65 g, 11.0 mmol) in dichloromethane (30 mL) was stirred at room temperature. After 25 minutes, the temperature was lowered to 0° C. and a solution of amine 24 (~10.0 mmol) in dichloromethane (20 mL) was added slowly. After 1 h at 0° C. the reaction mixture was diluted with ethyl acetate and washed with 5% aqueous citric acid followed by brine. The organic layer was dried (Na$_2$SO$_4$) and concentrated. The crude residue was purified by flash column chromatography (SiO$_2$: gradient 20 to 40% ethyl acetate in hexane) to yield 25 (2.92 g, 68%, ~1:1 mixture of diastereomers) as a white solid. ES (+) MS m/e=432 (M+1).

c) A mixture of 25 (400 mg, 0.930 mmol), 4-benzyloxy-benzeneboronic acid (424 mg, 1.86 mmol), Pd(dppf)Cl$_2$ dichloromethane complex (37.2 mg, 0.0465 mmol), and 1 M aqueous K$_2$CO$_3$ (1.86 mL, 1.86 mmol) in dioxane was heated at 105° C. until LC/MS indicated complete conversion. After cooling to room temperature, the reaction was diluted with ethyl acetate and the phases were separated. The organic layer was dried (Na$_2$SO$_4$), filtered through a plug of celite, and concentrated. The ester 26 was used directly in the next step without further purification. ES (+) MS m/e=534 (M+1).

d) To a suspension of 26 (~0.930 mmol) and Pd/C (790 mg, 0.372 mmol, Degussa type E101 NE/W, 10% Pd (dry basis) on activated-carbon, wet. Water ~50%) in ethanol (6.2 mL) was added ammonium formate (470 mg, 7.44 mmol). The resulting mixture was heated at 70° C. until LC/MS indicated exhaustive reduction (usually ~0.5 h). After cooling to room temperature, the mixture was filtered through a plug of celite and concentrated. The residue was dissolved in ethyl acetate and washed with aqueous 0.5 N HCl and brine. The organic layer was dried (Na$_2$SO$_4$) and concentrated to yield 27 (294 mg, 89% for two steps) of a crude oil that was used without further purification. ES (+) MS m/e=356 (M+1).

e) Resin 3 (400 mg, ~0.16 mmol) was treated with 20% piperidine in DMF (5 mL) for 30 min at room temperature. The resin was drained and washed with DMF (10×5 mL). To the resin in DMF (4 mL) was added 21 (177 mg, 0.5 mmol), PyBOP (520 mg, 1.0 mmol) and diisopropylethylamine (350 µL, 4.0 mmol). The reaction mixture was shaken overnight at room temperature, drained, and then washed with DMF (5×5 mL) and CH$_2$Cl$_2$ (5×5 mL).

The resin was treated with THF/AcOH/acetaldehyde/TFA (4 mL, 5:1:1:0.25), shaken at room temperature for 3 h, and then filtered and washed with CH$_2$Cl$_2$ (2×4 mL). The combined filtrate was concentrated to dryness under reduced pressure. The resulting residue was treated with TFA/CH$_2$Cl$_2$ (3 mL, 1:1). The solution was stirred at room temperature for 1 h and the solvent was removed under reduced pressure. The crude residue was purified by reverse-phase HPLC to yield 28. ES (+) MS m/e=455 (M+H).

Example 18

Synthesis of 3-[6-(3,4-dimethyl-benzoylamino)-2-(4-isopropyl-phenyl)-hexanoylamino]-4-oxo-butyric acid

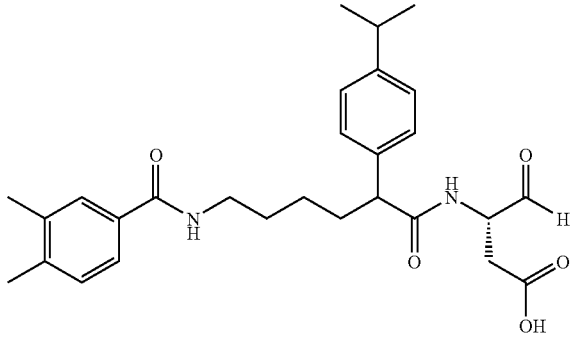

29

The title compound 29 was prepared according to Example 17c–e except for using 4-isopropylbenzeneboronic acid instead of 4-benzyloxybenzeneboronic acid. ES (+) MS m/e=481 (M+1).

Example 19

Synthesis of 3-[6-(3,4-dimethyl-benzoylamino)-2-pyrid-3-yl-hexanoylamino]-4-oxo-butyric acid

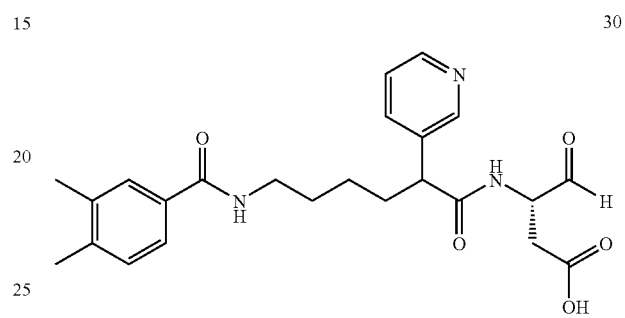

30

Compound 30 was prepared according to Example 17c–e except for using pyridine-3-boronic acid instead of 4-benzyloxybenzeneboronic acid. ES (+) MS m/e=440 (M+1).

Example 20

Synthesis of 3-[2-(4-acetylamino-phenyl)-6-(3,4-dimethyl-benzoylamino)-hexanoylamino]-4-oxo-butyric acid

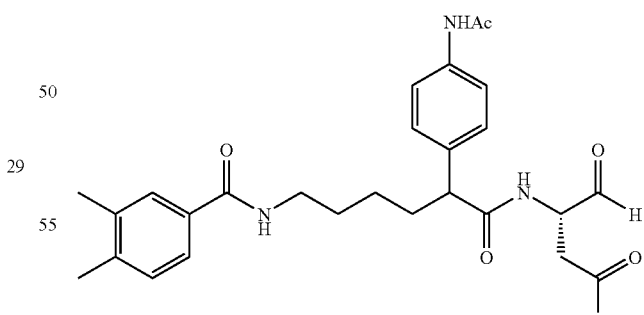

31

Compound 31 was prepared according to Example 17c–e except for 4'-(4,4,5,5-tetramethyl-1,3,2-dioxaborolan-2-yl)-acetanilide instead of 4-benzyloxybenzeneboronic acid. ES (+) MS m/e=496 (M+1).

Example 21

Synthesis of 3-[6-(3,4-dimethyl-benzoylamino)-2-(5-methyl-thien-2-yl)-hexanoylamino]-4-oxo-butyric acid

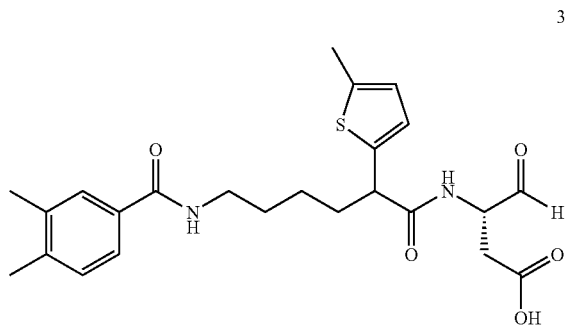

32

Compound 32 was prepared according to Example 17c–e except for using 5-methyl-2-thiophene-boronic acid instead of 4-benzyloxybenzeneboronic acid. ES (+) MS m/e=459 (M+1).

Example 22

Synthesis of 3-[2-benzofuran-2-yl-6-(3,4-dimethyl-benzoylamino)-hexanoylamino]-4-oxo-butyric acid

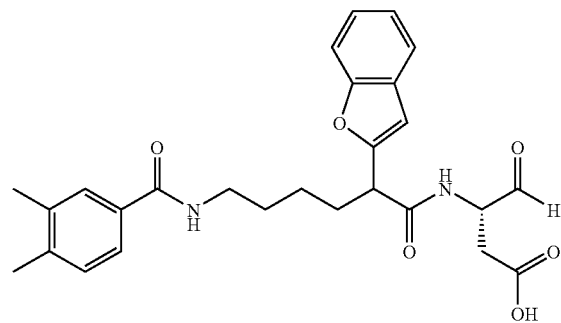

33

Compound 33 was prepared according to Example 17c–e except for using 2-benzofuranboronic acid instead of 4-benzyloxybenzeneboronic acid. ES (+) MS m/e=479 (M+1).

Example 23

Synthesis of 3-{6-[(benzooxazole-5-carbonyl)-amino]-2-phenyl-hexanoylamino}-4-oxo-butyric acid

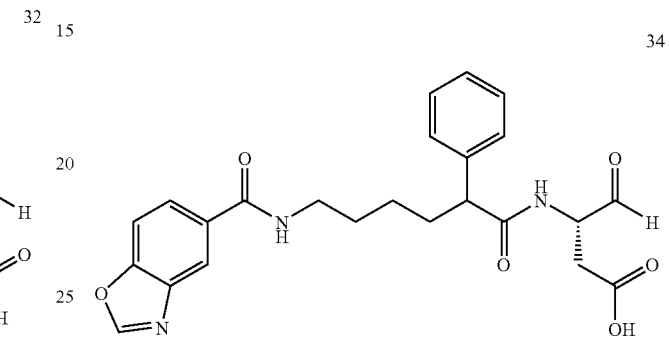

34

Compound 34 was prepared according to Example 17b–e except for using benzoxazole-5-carboxylic acid as a reagent instead of 3,4-dimethylbenzoic acid and phenylboronic acid as a reagent instead of 4-benzyloxybenzeneboronic acid. ES (+) MS m/e=452 (M+1).

Example 24

Synthesis of 5-[5-(1-carboxymethyl-2-oxo-ethylcarbamoyl)-5-phenyl-pentylsulfamoyl]-2-hydroxy-benzoic acid

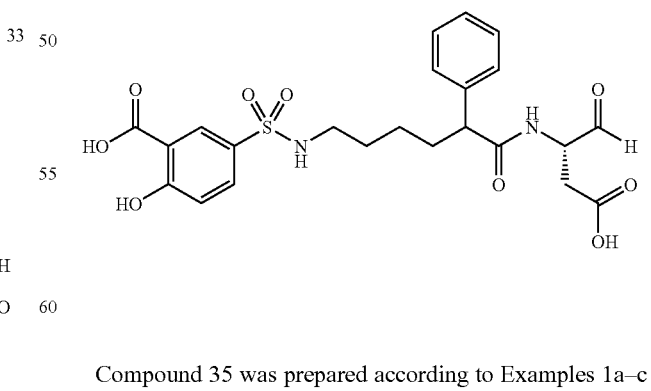

35

Compound 35 was prepared according to Examples 1a–c and 11a–c except for using methyl phenylacetate as a reagent instead of ethyl-2-thiopheneacetate and 5-chlorosulfonyl-2-hydroxy benzoic acid as a reagent instead of o-tolylsulfonyl chloride. ES (+) MS m/e=507 (M+1).

Example 25
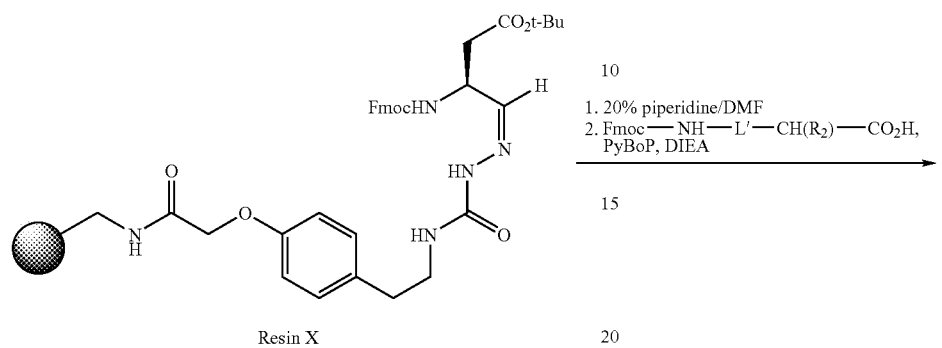

L' is part of the linker L that includes —C(=O)NH— in this illustration.

General Procedure for Synthesis of Aspartyl Aldehyde Caspase-1 Inhibitors on Solid Support The Fmoc-aldehyde resin X (approximately 0.25 mmol/g resin) was prepared using the procedure of Karanewsky et al. in WO 00/23421. A portion of this resin (300 mg, 0.075 mmol) was weighed into a vessel for solid-phase reactions. A solution (3 mL) of 20% piperidine in DMF was added, and the mixture was agitated for 30 minutes on an orbital shaker. The solvent was then removed by filtration, and the resin was washed with 3×4 mL DMF, then with 3×4 mL dichloromethane, then with 3×4 mL diethyl ether. The resin was dried briefly by continuing the vacuum filtration 15 minutes.

To the reaction vessel were added DMF (3 mL), the Fmoc-protected carboxylic acid linker (0.150 mmol, 2 eq), DIEA (78 µL, 0.45 mmol, 6.0 eq), and PyBoP (117 mg, 0.225 mmol, 3 eq). The vessel was capped and agitated overnight. The solvent was then removed by vacuum filtration, and the resin washed as before. The resin was then treated as before with 20% piperidine in DMF, to cleave the Fmoc protecting group from the linker, followed by filtration and washing of the resin as before.

To the vessel were then added DMF (3 mL), the P4 carboxylic acid (0.150 mmol, 2 eq), DIEA (78 mL, 0.45 mmol, 6.0 eq), and PyBoP (117 mg, 0.225 mmol, 3 eq). The vessel was then capped and agitated overnight, followed by filtration and washing of the resin as before.

A clevage solution consisting of THF (15 mL), acetic acid (3 mL), trifluoroacetic acid (0.75 mL), and acetaldehyde (3 mL) was freshly prepared. A 3 mL portion of this solution was added to the reaction vessel, and the vessel was tightly capped (to prevent leakage under pressure of the isobutylene liberated by the reaction), and the vessel agitated for 2 hours. The solvent was then collected by filtration, and the resin washed with dichloromethane. The combined organic solution was then concentrated by rotary evaporation followed by 30 minutes under high vacuum, yielding the free aldehyde with the t-butyl ester intact.

The t-butyl ester was suspended in dichloromethane (1 mL), and trifluoroacetic acid (1 mL) was added. After 30 minutes, the reactions were concentrated and purified by reverse phase HPLC in acetonitrile/water, providing the desired products as the trifluoroacetate salts.

Example 26

Synthesis of 4-oxo-3-{6-[4-(quinoxalin-2-ylamino)-benzoylamino]-hexanoylamino}-butyric acid

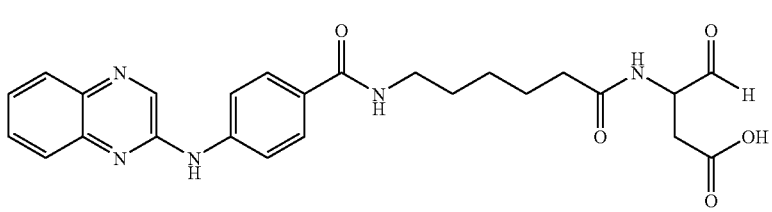

36

Compound 36 was prepared starting with 302 mg resin, 54.3 mg Fmoc-6-aminohexanoic acid, 118 mg PyBoP, and 78 µL DIEA for the coupling of the linker onto the resin. The coupling of the tricyclic acid was accomplished using 38.1 mg of the acid, 118 mg PyBoP, and 78 µL DIEA. This procedure resulted in 11.8 mg of purified product as the TFA salt.

Example 27

Synthesis of 4-oxo-3-[2-(5-{[4-(quinoxalin-2-ylamino)-benzoylamino]-methyl}-thiophen-2-yl)-acetylamino]-butyric acid

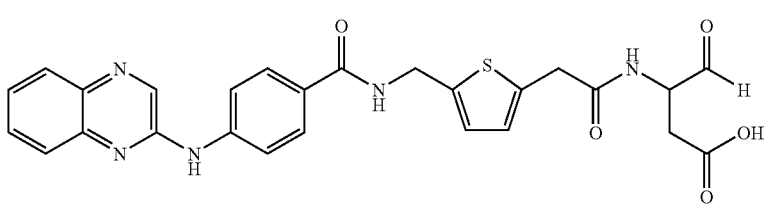

37

Compound 37 was prepared starting with 297 mg resin, 46.5 mg linker acid, 126 mg PyBOP, and 78 µL DIEA for the coupling of the linker onto the resin. The synthesis of the N-Fmoc-5-aminomethyl-2-thiphenylacetic acid has been described elsewhere. The coupling of the tricyclic acid was accomplished using 38.4 mg of the acid, 118 mg PyBoP, and 78 μL DIEA. This procedure resulted in 12.1 mg of purified product as the TFA salt.

Example 28

Synthesis of 4-oxo-3-{6-[4-(quinoxalin-2-ylamino)-benzoylamino]-2-thiophen-2-yl-hexanoylamino}-butyric acid

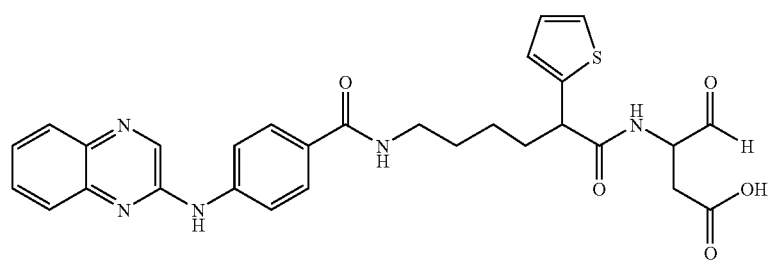

38

Compound 38 was prepared starting with 304 mg resin, 65 mg linker acid, 121 mg PyBoP, and 78 μL DIEA for the coupling of the linker onto the resin. The synthesis of the N-Fmoc-6-amino-2-(2-thienyl)hexanoic acid has been previously described. The coupling of the tricyclic acid was accomplished using 40.3 mg of the acid, 118 mg PyBoP, and 78 μL DIEA. This procedure resulted in 7.0 mg of purified product as the TFA salt.

Example 29

Caspase-1 Activity Assay

The effectiveness of compounds against the activity of human recombinant caspase-1 (BIOMOL Research Laboratories, Inc.) was measured using fluorescent based assays. 3 nM active enzyme was added to test compounds dissolved in DMSO and incubated at room temperature for 30 minutes. The tetrapeptide substrate (Ac-Trp-Glu-His-Asp-AFC, Alexis Biochemicals) was added to a final concentration of 4 μM to initiate the reaction, bringing the final reaction volume to 50 μL. Preferred caspase-1 reaction buffer contained 25 mM HEPES pH 7.4, 0.1% CHAPS, 50 mM KCl and 5 mM β-mercaptoethanol (β-ME). Caspase activity was monitored using Molecular Devices' Microplate Spectrofluorometer Gemini XS over 15-minutes at room temperature. $IC_{50}$ values were calculated using direct fits of the data to a 4-parameter fit using the computer application SOFTmax PRO. $K_{i(apparent)}$ values were calculated according to Kuzmic et al. 2000 (*Analytical Biochem.* 286:45–50).

Example 30

PBMC Isolation and IL-1 Assay

Blood (obtained from the Stanford blood Bank) was diluted 1:1 in sterile PBS, mixed by inversion, and overlayed over 1 volume of Ficoll in a sterile centrifuge tube. After centrifuging at ~400 g for 30 min at ambient temperature the peripheral blood mononuclear cell (PBMC) layer was removed and transferred to a sterile centrifuge tube. Cells were washed twice with PBS and resuspended in RPMI 1640 media containing 10% FBS (Gibco 11875-093). Mononuclear cells were counted and diluted to a final concentration of $1.2 \times 10^6$ cells/mL. 100 μL (~$1.2 \times 10^5$ cells) of the cell suspension was added to each well in a 96 well plate, incubated at 37° C. for 4 hr, and supernatant containing nonadherent cells removed and replaced with 170 μL fresh media. Serial dilutions of test compounds were added to the adherent cells so the final concentration of DMSO remained constant at 0.2%, and 10 μl of LPS (Sigma, L4391) immediately added to a final concentration of 0.5 ng/ml. Plates are then incubated an additional ~18 hr at 37° C., at which point 170 μl of supernatant (containing secreted IL-1β) was removed. IL-1β protein levels in the supernatant (diluted as necessary) were quantitated with an ELISA based assay (MAB601, monoclonal anti-human IL-1β antibody, and BAF201, biotinylated anti-human IL-1β antibody; both used according to R+D Systems supplied protocol).

Example 31

Mutagenesis and Expression of Human Caspase-1

Human caspase-1 is a cysteine protease that is active as a tetramer composed of two heterodimers. Each heterodimer contains a large subunit and a small subunit, which are also referred to as p20 and p10, respectively. The sequence of the caspase-1 precursor is shown as SEQ ID NO:1. Residues 1–119 of SEQ ID NO:1 correspond to the propeptide region and residues 120–404 correspond to the mature chain. The p20 and p10, subunits, corresponding to residues 120–297 of SEQ ID NO:1 (large subunit) and residues 317–404 of SEQ ID NO:1 (small subunit), respectively, can be derived from autocatalysis of either the caspase-1 precursor or caspase-1 mature chain. Alternatively, as described below, the large and small subunits of caspase-1 may each be expressed separately, and then recombined to form the tetramer.

MADKVLKEKR KLFIRSMGEG TINGLLDELL QTRV-
LNKEEM EKVKRENATV MDKTRALIDS VIPKGAQ-
ACQ ICITYICEED SYLAGTLGLS ADQTSGNYLN
MQDSQGVLSS FPAPQAVQDN PAMPTSSGSE
GNVKLCSLEE AQRIWKQKSA EIYPIMDKSS RTR-
LALIICN EEFDSIPRRT GAEVDITGMT MLLQN-
LGYSV DVKKNLTASD MTTELEAFAH RPEHKTS-
DST FLVFMSHGIR EGICGKKHSE QVPDILQLNA
IFNMLNTKNC PSLKDKPKVI IQACRGDSP GVVW-
FKDSVG VSGNLSLPTT EEFEDDAIKK AHIEKD-
FIAF CSSTPDNVSW RHPTMGSVFI GRLIEHMQEY

ACSCDVEEIF RKVRFSFEQP DGRAQMPTTE RVTL-
TRCFYL FPGH SEQ ID NO:1

An inactive variant of caspase-1 having the active site cysteine (corresponding to C285 in SEQ ID NO:1) mutated to alanine in each of the large subunits was also produced. The sequence of the large subunit containing the active site mutation is shown here as SEQ ID NO:2. Both wildtype and the C285A mutant of human caspase-1 are referred herein as "human caspase-1". Mutagenesis of the large subunit, and expression and refolding of wild-type and mutant subunits are described herein.

NPAMPTSSGS EGNVKLCSLE EAQRIWKQKS AEIYP-
IMDKS SRTRLALIIC NEEFDSIPRR TGAEVDITGM
TMLLQNLGYS VDVKKNLTAS DMTTELEAFA
HRPEHKTSDS TFLVFMSHGI REGICGKKHS EQVP-
DILQLN AIFNMLNTKN CPSLKDKPKV
IIIQAARGDS PGVVWFKD SEQ ID NO:2

Caspase-1 Active Site Cysteine-Alanine Mutagenesis

The active site cysteine in the large subunit of caspase-1 was mutated by a PCR reaction performed with the Quick Change Kit from Stratagene using the manufacturer's protocol. In short, PCR reactions contained a pRSET expression plasmid encoding the large subunit, a forward primer (SEQ ID NO:3) and a reverse primer (SEQ ID NO:4). Specifically, 2 μL of the plasmid was combined in a reaction mixture with 1.25 μL of each of two primers, along with 1 μL 2.5 mM dNTPs, 5 μL 10X buffer, 39.5 μL water, and 1 μL pfu-turbo polymerase. Sequences of SEQ ID NO:3 and SEQ ID NO:4 are as shown.

CATCATCCAGGCCGCCCGTGGTGACAGCC SEQ ID NO:3
GGCTGTCACCACGGGCGGCCTGGATGATG SEQ ID NO:4

The PCR reaction was first incubated at 95° C. for 1 min, and then allowed to undergo 16 cycles of: 95° C. for 30 sec, 55° C. for 60 sec, 68° C. for 780 sec. After PCR, the product was digested with 1 μL Dpn-1 at 37° C. for 1 hr, and 1 μL of the digested mixture was used to transform E. coli. The following procedure was used for the transformation. Ultracompetent Gold XL1-Blue cells (Stratagene) were thawed on ice, and 50 μL of cells were added to a chilled reaction tube containing the 1 μL digested DNA. The resulting mixture of cells and DNA was kept on ice for 30 min, subjected to heat shock for 45 sec, and then allowed to recover on ice for 2 min. Next, 0.5 mL of SOC (media) was added to the tube, which was then incubated for 1 hr at 37° C. A portion of the transformed cells (250 μL) was spread on plates containing 100 μg/mL, and the plates were incubated overnight at 37° C. Single, isolated colonies were picked, and grown overnight in 3 mL cultures. Mutagenized plasmid DNA, resulting from in vivo recombination and subsequent amplification, was isolated from the cells by Qiagen DNA miniprep kits. Plasmid DNA was sequenced to verify that the correct plasmid encoding the mutated large subunit of caspase-1 was obtained.

Protein Expression and Isolation of Inclusion Bodies

The small subunit, large subunit, and mutated large subunit of human caspase-1 were each expressed from a separate plasmid as follows. A plasmid encoding a caspase-1 subunit was used to transform bacterial expression cells. The transformed cells were grown overnight in a small culture; subsequently, a portion of the small culture was used to inoculate a large culture of 1.5 L. The 1.5 L culture was grown until OD=1.0, at which time the cells were induced with 1 mM IPTG and allowed to grow for 3 hrs. The cells were harvested and inclusion bodies were isolated therefrom as follows. Cells were centrifuged at 5000 rpm for 15 min, washed once with 500 mL 1X PBS, and then centrifuged again. The cell pellet was resuspended in 20 mL of 50 mM HEPES pH 8.0, 300 mM NaCl, 1 M guanidine, 5 mM DTT. After micofluidizing the suspension 4 times, triton-x100 was added to 1% of the final volume, and mixed thoroughly. The resulting mixture was incubated on ice for 5 min, and then centrifuged at 16,000 rpm in a SS-34 rotor for 20 min. After removal of the supernatant, the pellet containing the inclusion bodies was resuspended in 25 mL of 50 mM HEPES pH 8.0, 300 mM NaCl, 1 M guanidine, 5 mM DTT, 1% triton x-100, using sonication until the pellet was completely dissolved. The resuspended mixture was centrifuged at 16,000 rpm for 15 min, and the pellet isolated by removal of the supernatant. Subsequently, the pellet was resuspended in 25 mL of 50 mM HEPES pH 8.0, 300 mM NaCl, 1 M guanidine, 5 mM DTT without triton x-100, using sonication until the pellet was completely dissolved. The resuspended mixture was centrifuged at 16,000 rpm for 15 min. Again, the pellet was isolated, resuspended in the 50 mM HEPES pH 8.0, 300 mM NaCl, 1 M guanidine, 5 mM DTT without triton x-100, and centrifuged at 16,000 rpm. The supernatant was removed, and the pellet resuspended a final time in 10 mL 6 M guanidine, 20 mM DTT. The resulting 6 M guanidine suspension was sonicated until the pellet was completely dissolved, and centrifuged at 16,000 rpm for 15 min. Protein was located in the supernatant. The concentration of protein was measured, and the protein was aliquoted into 6 mg portions, which were frozen.

Example 32

Renaturation of Wildtype Human Caspase-1

Protocol 1.

The 6M guanidine-HCl-solubilized fractions of caspase-1 (6 mg of p20 and 3 mg of p10) were combined in a 100-ml beaker. After stirring the fractions vigorously for approximately 30 seconds, 50 mls of renaturation buffer was added. The renaturation buffer comprises: 50 mM HEPES, pH 8.0 (although HEPES or Tris-HCL at pH 7–8.5 produces comparable results); 100 mM NaCl; 10% sucrose; 0.1% CHAPS; 10 mM DTT; and inhibitor resulting in a final inhibitor concentration of 20 μM. The resulting solution was stirred at room temperature for 6–18 hours, spun down in a Sorvall rotor for 30 minutes at 17,000 rpm to remove precipitates, and the clear supernatent was dialyzed overnight at 4° C. in a 10-kD MWCO membrane against 4 L of buffer composed of 50 mM sodium acetate pH 5.9, 50 mM NaCl, 5% glycerol and 4 mM DTT. Following dialysis, the preparation was centrifuged and the protein was either concentrated if no further purification was warranted, or purified on an S Sepharose column as the non-proteolyzed complex.

Protocol 2.

This method is the same as protocol 1 except that the renaturation buffer comprises: 50 mM HEPES, pH 8.0 (although HEPES or Tris-HCL at pH 7–8.5 produces comparable results); 100 mM NaCl; 1 M non-detergent sulfobetaine 201 [NDSB-201]; 10 mM DTT; and inhibitor resulting in a final inhibitor concentration of 20 μM.

Example 33

Purification of Renatured Human Caspase-1

Renatured caspase-1 was purified in a single step on an S Sepharose column. The protein was loaded onto a column that was preequilibrated with a buffer composed of 50 mM sodium acetate pH 5.9; 50 mM NaCl; and 5% glycerol. The column was washed with the equilibration buffer, and the intact caspase-1 p10/p20 complex was eluted from the column with increasing concentrations of NaCl (salt gradient between 50 and 1000 mM NaCl in a buffer containing 50 mM sodium acetate pH 5.9 and 5% glycerol). Because only the complex composed of non-proteolyzed subunits binds to S Sepharose, it can be easily separated from the partially proteolyzed population of protein molecules. If excess p20 is present, p20 may also bind to S Sepharose but this does not complicate the purification because p20 elutes at a higher salt concentration than the complex.

Example 34

Concentrating Caspase-1 and Storage

Final purified or unpurified samples were concentrated to 2–8 mg/ml, and snap-frozen in 50-μM aliquots in dry-ice/ethanol baths. Protein is stored at −80° C. The protein buffer composed of 50 mM sodium acetate pH 5.9, 50–100 mM sodium chloride, 4 mM DTT and 5% glycerol.

Example 35

Crystallization of Wildtype Caspase-1

Drops are set up on a cover slip with 1 μl each of a protein prep at 2–5 mg/ml and mother liquor containing 0.1 M PIPES pH 6.0, 2 mM magnesium chloride, 3 mM sodium azide, 10 mM DTT, 70–300 mM ammonium sulfate or lithium sulfate, and 20–30% polyethylene glycol 2000 [PEG 2000] monomethyl ether. Crystals are grown on 24-well Falcon tissue-culture plates over a reservoir containing 300 μl mother liquor by hanging-drop vapor diffusion at 4° C. Crystals appear within 12–36 hrs of setting up plates and grow to a diffraction-quality size within 1–5 days.

Example 36

Crystallization of the Active-Site Cys285→Ala Mutant of Caspase-1

Mutant caspase 1 was renatured using protocol 2 (Example 32). Crystals were produced in 1.5–2.0 M sodium malonate pH 7 and diffraction-quality crystals of apo human caspase-1 grew by hanging-drop vapor diffusion at 4° C. within a week.

What is claimed:

1. A compound of the formula

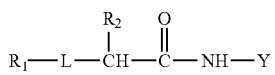

wherein:
R$_1$ is chosen from optionally substituted aryl, optionally substituted aralkyl, optionally substituted heteroaryl, and optionally substituted heteroaralkyl;

L is a linker selected from the group consisting of —(CH$_2$)$_m$—O—(CH$_2$)$_n$—; —(CH$_2$)$_m$—NR—(CH$_2$)$_m$—; —(CH$_2$)$_m$—NRCONR—(CH$_2$)$_n$—; (CH$_2$)$_m$—NRCOO—(CH$_2$)$_n$—; —(CH$_2$)$_m$—CONR—(CH$_2$)$_n$—; —(CH$_2$)$_m$—NRCO—(CH$_2$)$_n$—; —(CH$_2$)$_m$—NRSO$_2$—(CH$_2$)$_n$—; —(CH$_2$)$_m$—CO—(CH$_2$)$_n$—; —(CH$_2$)$_m$—NRCONRSO$_2$—(CH$_2$)$_n$—; —(CH$_2$)$_m$—NRCONRCO—(CH$_2$)$_n$—; —(CH$_2$)$_m$—SO$_2$—(CH$_2$)$_n$—; —(CH$_2$)$_m$—SO$_2$CH$_2$CO—(CH$_2$)$_n$—; —(CH$_2$)$_m$—SO$_2$NR—(CH$_2$)$_n$—; —(CH$_2$)$_m$—SCH$_2$CO—(CH$_2$)$_n$— and —Z—(CH$_2$)$_m$—Ar—(CH$_2$)$_n$— where Z is —C(=O)NH—, —NHC(=O)—, or —SO$_2$NH—, Ar is a 5 membered heroarylene, m and n are each 0, 1, 2, 3, 4, or 5, and wherein R is each independently hydrogen, C$_1$–C$_5$ alkyl, C$_1$–C$_5$ hydroxyalkyl, or C$_1$–C$_5$ alkylhalide;

R$_2$ is chosen from H, optionally substituted aryl, optionally substituted aralkyl, optionally substituted heteroaryl, and optionally substituted heteroaralkyl; and Y is

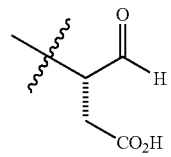

or single stereoisomers, mixtures of stereoisomers, or the pharmaceutically acceptable salts, amides, or esters thereof.

2. The compound as defined in claim 1, wherein L is a linker that places the R$_1$ group at a distance of about 6 Å–15 Å from the —CH(R$_2$)—CO—NH—Y group.

3. The compound defined in claim 2, wherein the distance is about 7 Å–12 Å.

4. The compound defined in claim 2, where the distance is about 8 Å–10 Å.

5. The compound of claim 1 where L is —(CH$_2$)$_m$—CONR—(CH$_2$)$_n$— and m and n are each 0, 1, 2, 3, or 5.

6. The compound of claim 1 where L is —(CH$_2$)$_m$—NRCO—(CH$_2$)$_n$— and m and n are each 0, 1, 2, 3, or 5.

7. The compound of claim 1 where L is —(CH$_2$)$_m$—NRSO$_2$—(CH$_2$)$_n$— and m and n are each 0, 1, 2, 3, or 5.

8. The compound of claim 1 where L is —(CH$_2$)$_m$—SO$_2$NR—(CH$_2$)$_n$— and m and n are each 0, 1, 2, 3, or 5.

9. The compound of claim 1 wherein L is —Z—(CH$_2$)$_m$—Ar—(CH$_2$)$_n$— where Z is —C(=O)NH—, —NHC(=O)—, or —SO$_2$NH—; m and n are each 0, 1, 2, or 3; and Ar is a 5 membered heroarylene.

10. The compound defined in claim 1 selected from

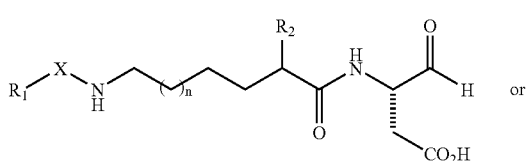

-continued

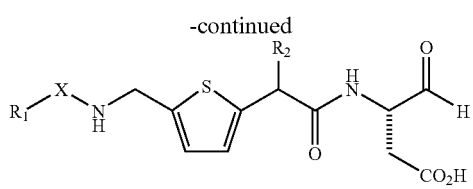

wherein:
R₁ is chosen from optionally substituted aryl, optionally substituted aralkyl, optionally substituted heteroaryl, and optionally substituted heteroaralkyl;
R₂ is chosen from H, optionally substituted aryl, optionally substituted aralkyl, optionally substituted heteroaryl, and optionally substituted heteroaralkyl;

X is —(CO)— or —(SO₂)—; and n is 0 or 1;

or single stereoisomers, mixtures of stereoisomers, or the pharmaceutically acceptable salts, amides, or esters thereof.

11. The compound of claim 10, wherein X is —(CO)—.
12. The compound of claim 10, wherein n is 1.
13. The compound of claim 10, wherein R₁ is optionally substituted aryl or optionally substituted heteroaryl.
14. The compound of claim 11, wherein R₁ is chosen from optionally substituted phenyl, optionally substituted naphthyl, optionally substituted pyridinyl, optionally substituted quinolinyl, optionally substituted thiophenyl, optionally substituted oxazolyl, optionally substituted 2,3-dihydrobenzo[b]thiophen-2-yl, and optionally substituted quinoxalinyl.
15. The compound defined in claim 12, where R₁ is dimethylphenyl, tolyl methyl, quinoxalinyl, tolyl cyclopentyl, morpholinylpyridyl, napthalenyl, chloro benzo[b]thienyl, amino dichlorophenyl, quinolinyl, phenyloxazolyl, tolyl, thienyl, trifluoro acetyl tetrahydro isoquinolinyl, pyridyl thienyl, fluoro chloro carboxy phenyl, hydroxy carboxy phenyl, benzooxazolyl, or quinoxalinyl amino phenyl.
16. The compound of claim 14, wherein R₂ is chosen from optionally substituted thiophenyl, optionally substituted phenyl, optionally substituted pyridinyl, and optionally substituted benzofuranyl.
17. The compound of claim 16, wherein R₂ is selected from the group consisting of H, thienyl, preferably 2-thienyl, alkyl thienyl, preferably 3-methyl 2-thienyl, phenoxy, preferably 4-phenoxy, phenyl, alkylphenyl, preferably 4-isopropyl phenyl, acetylaminophenyl, preferably 4-acetylaminophenyl, pyridyl, preferably 3-pyridyl, and benzooxazole.
18. The compound of claim 1 selected from the group consisting of:

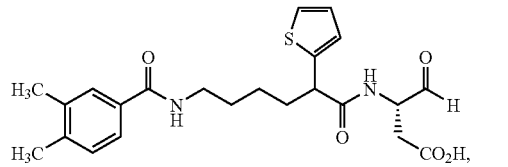

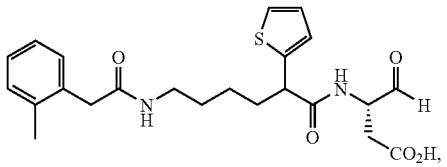

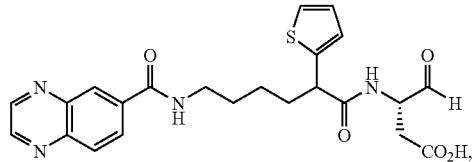

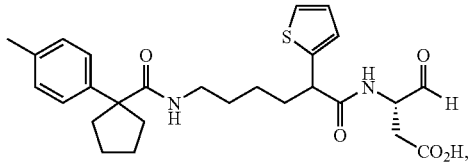

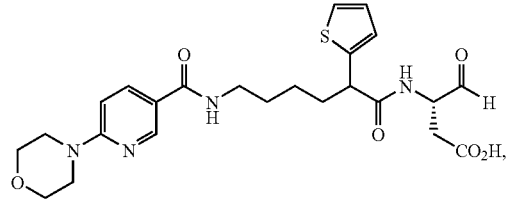

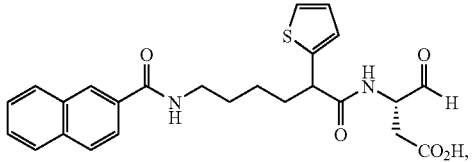

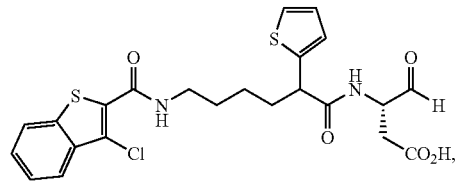

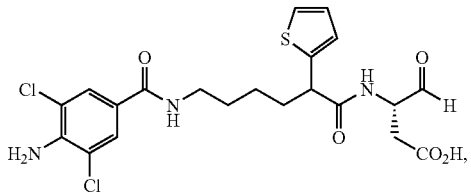

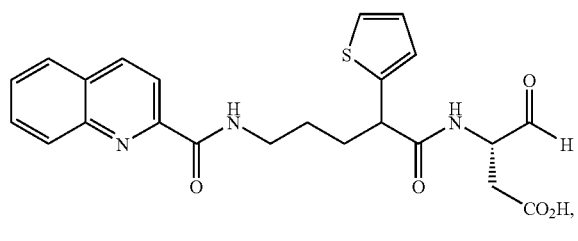

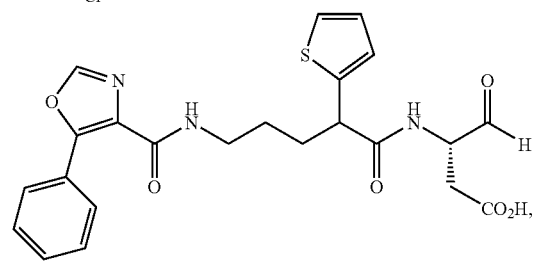

-continued
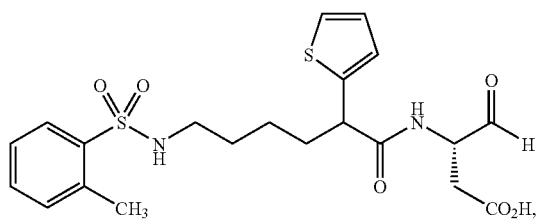
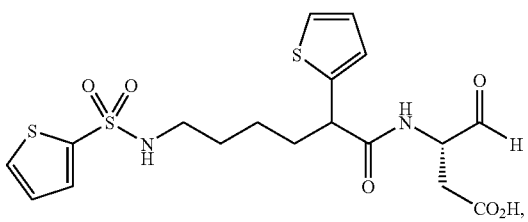
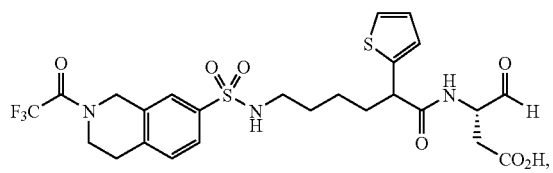
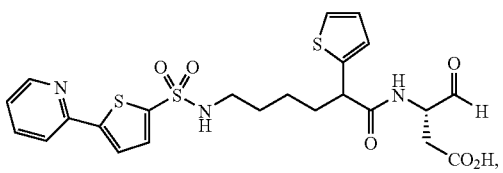
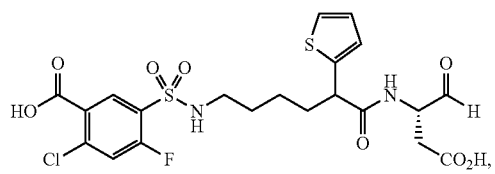
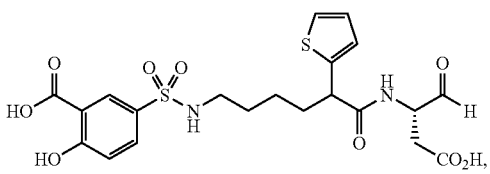
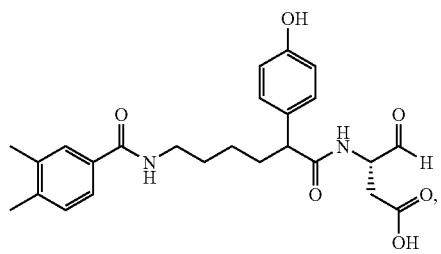
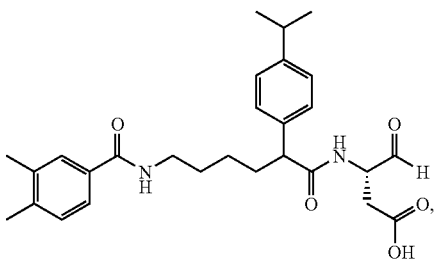
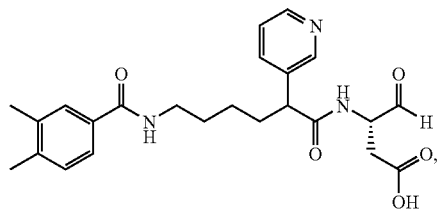
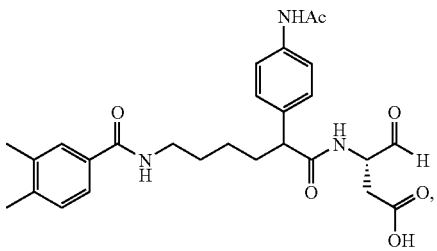
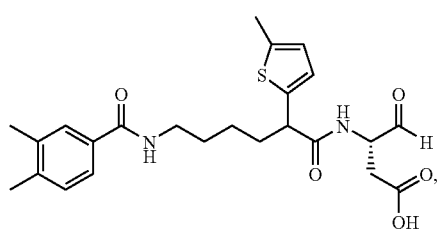
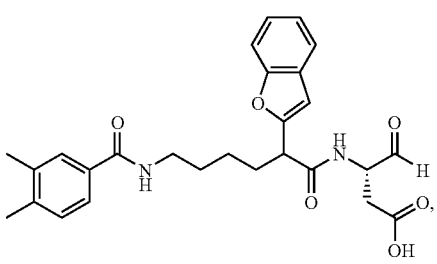
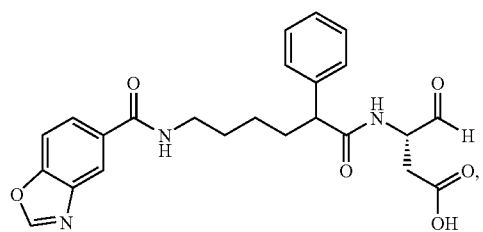
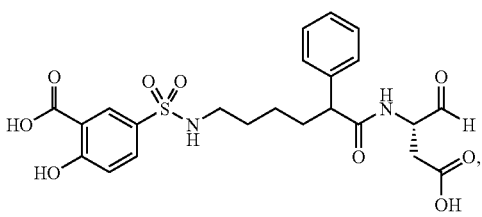

-continued
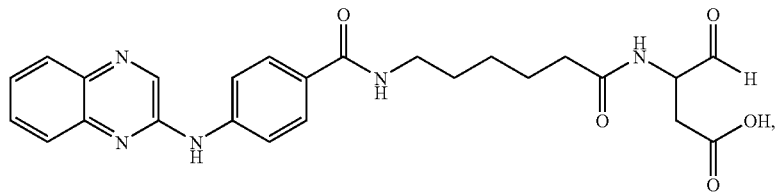
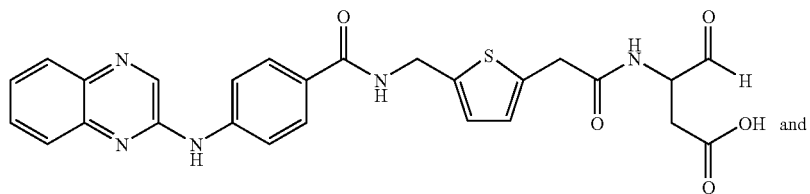
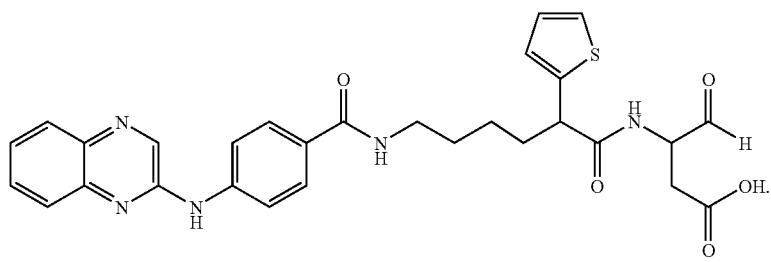
19. The compound defined in claim 18 selected from the group consisting of
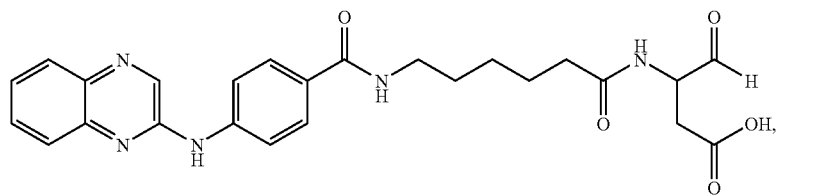
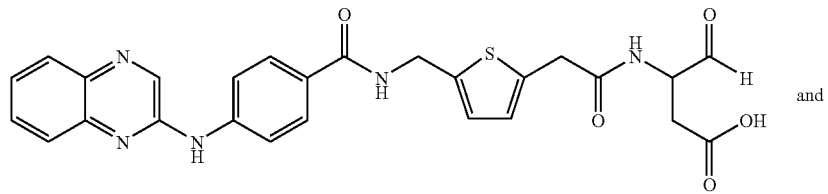
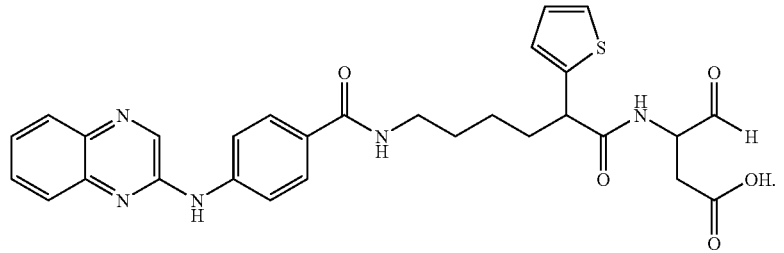

20. A pharmaceutical composition comprising a therapeutically effective amount of a compound of claim 1; and a pharmaceutically acceptable excipient.

21. A method of treating inflammation in an animal having a disease or condition that would benefit from treatment by administration of a caspase-1 inhibitor, comprising administering to said animal a therapeutically effective amount of compound of claim 1.

* * * * *